(12) United States Patent
Thompson et al.

(10) Patent No.: US 10,046,097 B2
(45) Date of Patent: Aug. 14, 2018

(54) APPARATUS AND METHODS FOR COMPRESSING A WOMAN'S BREAST TO EXPRESS MILK IN A CONCEALABLE MANNER

(71) Applicant: DS Labs, Inc., Canton, MA (US)

(72) Inventors: Susan Thompson, Canton, MA (US); Andrew Thompson, Canton, MA (US); Chinawut P. Paesang, Cumberland, RI (US); Casper Crouse, Taunton, MA (US); Elizabeth Nelson, Wellesley, MA (US)

(73) Assignee: DS Labs, Inc., Canton, MA (US)

( * ) Notice: Subject to any disclaimer, the term of this patent is extended or adjusted under 35 U.S.C. 154(b) by 0 days.

(21) Appl. No.: 14/311,896

(22) Filed: Jun. 23, 2014

(65) Prior Publication Data

US 2014/0378946 A1    Dec. 25, 2014

Related U.S. Application Data

(60) Provisional application No. 61/838,220, filed on Jun. 21, 2013, provisional application No. 61/838,223,
(Continued)

(51) Int. Cl.
*A61M 1/06* (2006.01)
*A41C 3/04* (2006.01)
(Continued)

(52) U.S. Cl.
CPC .............. *A61M 1/062* (2014.02); *A41C 3/04* (2013.01); *A61M 1/06* (2013.01); *A61H 9/0078* (2013.01);
(Continued)

(58) Field of Classification Search
CPC ...... A61M 1/06–1/068; A61M 1/0031; A61M 1/007; A61M 2205/3646;
(Continued)

(56) References Cited

U.S. PATENT DOCUMENTS

| | | | |
|---|---|---|---|
| 4,270,538 A | 6/1981 | Murphy | |
| 5,897,580 A * | 4/1999 | Silver | A61F 7/03 128/889 |

(Continued)

FOREIGN PATENT DOCUMENTS

| | | |
|---|---|---|
| CN | 100367888 C | 2/2008 |
| GB | 2503703 A | 1/2014 |

(Continued)

OTHER PUBLICATIONS

International Search Report and Written Opinion for Application No. PCT/US2014/043645, dated Dec. 23, 2014 (21 pages).
(Continued)

*Primary Examiner* — Bhisma Mehta
*Assistant Examiner* — Jenna Zhang
(74) *Attorney, Agent, or Firm* — Nutter McClennen & Fish LLP; John J. Penny, Jr.

(57) ABSTRACT

Wearable breast pumps are provided which utilize compression to enhance milk expression. The breast milk expression systems herein can allow breastfeeding users to obtain milk discreetly and comfortably in the presence of others. These systems compress the breast at one or more locations, such as at a base of a breast and/or along inferior and lateral sides of a breast, to stimulate milk expression. Various components and methods for expressing milk can facilitate milk output. For example, vacuum can be used in conjunction with compression. For another example, one or more temperature sensitive components can be utilized to improve milk secretion. In some embodiments, milk can be collected
(Continued)

in a sterile custom storage container located around or beneath the breasts to facilitate wearability. After expression is complete, a quick-release valve can be used to detach the storage container from the pump and can prevent leaks.

14 Claims, 26 Drawing Sheets

Related U.S. Application Data filed on Jun. 21, 2013, provisional application No. 61/975,012, filed on Apr. 4, 2014.

(51) Int. Cl.
*A61M 1/00* (2006.01)
*A61H 9/00* (2006.01)
*A61H 23/02* (2006.01)

(52) U.S. Cl.
CPC ...... *A61H 23/02* (2013.01); *A61H 2201/0107* (2013.01); *A61H 2201/018* (2013.01); *A61H 2201/0207* (2013.01); *A61H 2201/165* (2013.01); *A61H 2201/5002* (2013.01); *A61H 2201/5005* (2013.01); *A61H 2201/5071* (2013.01); *A61H 2205/082* (2013.01); *A61M 1/0031* (2013.01); *A61M 2205/3382* (2013.01); *A61M 2205/3646* (2013.01); *A61M 2209/088* (2013.01)

(58) Field of Classification Search
CPC .... A61M 2209/088; A61M 2210/1007; A41C 3/04; A61H 9/0078; A61H 2205/082; A61H 23/02; A61H 2201/5002; A61H 2201/165; A61H 2201/0207; A61H 2201/018; A61H 2201/0107; A61H 2201/082; A61H 2201/5005; A61H 2201/5071
See application file for complete search history.

(56) References Cited

U.S. PATENT DOCUMENTS

| | | |
|---|---|---|
| 6,213,840 B1 | 4/2001 | Han |
| 6,227,936 B1 | 5/2001 | Mendoza |
| 6,247,996 B1* | 6/2001 | Fields ............... A41C 3/04 450/36 |
| 6,261,313 B1 | 7/2001 | MacWhinnie et al. |
| 6,358,226 B1 | 3/2002 | Ryan |
| 7,207,336 B1 | 4/2007 | Doiron |
| 8,057,425 B1 | 11/2011 | Myers et al. |
| 8,087,972 B2 | 1/2012 | Mutschler |
| 8,307,463 B2 | 11/2012 | Ritchie |
| 8,357,024 B2 | 1/2013 | Baker-Jackson |
| 2001/0031911 A1 | 10/2001 | Khouri |
| 2001/0044593 A1 | 11/2001 | Lundy |
| 2003/0211810 A1 | 11/2003 | Raimondo |
| 2004/0122356 A1* | 6/2004 | Burke .............. A61M 1/062 604/74 |
| 2005/0234370 A1* | 10/2005 | Beal ............... A61H 9/0078 601/15 |
| 2006/0106334 A1* | 5/2006 | Jordan ............ A61M 1/0027 604/74 |
| 2006/0270973 A1* | 11/2006 | Chu ............... A61H 9/0078 604/74 |
| 2008/0262420 A1* | 10/2008 | Dao ............... A61M 1/06 604/74 |
| 2011/0190695 A1 | 8/2011 | Thilwind et al. |
| 2011/0251552 A1* | 10/2011 | Brittner ............ A61M 1/06 604/74 |
| 2012/0277636 A1* | 11/2012 | Blondheim ........ A61B 5/11 600/595 |
| 2012/0315353 A1 | 12/2012 | Becsi et al. |
| 2013/0065485 A1 | 3/2013 | Goodwin et al. |
| 2014/0142501 A1* | 5/2014 | Clark ............. A61M 1/066 604/74 |
| 2014/0236072 A1* | 8/2014 | Zhang ............. A61M 1/06 604/23 |

FOREIGN PATENT DOCUMENTS

| | | |
|---|---|---|
| WO | 00/41745 A1 | 7/2000 |
| WO | 2004/026368 A2 | 4/2004 |
| WO | 2015/029029 A1 | 3/2015 |

OTHER PUBLICATIONS

Extended European Search Report for Application No. 14813342.4, dated Oct. 31, 2016 (7 pages).

* cited by examiner

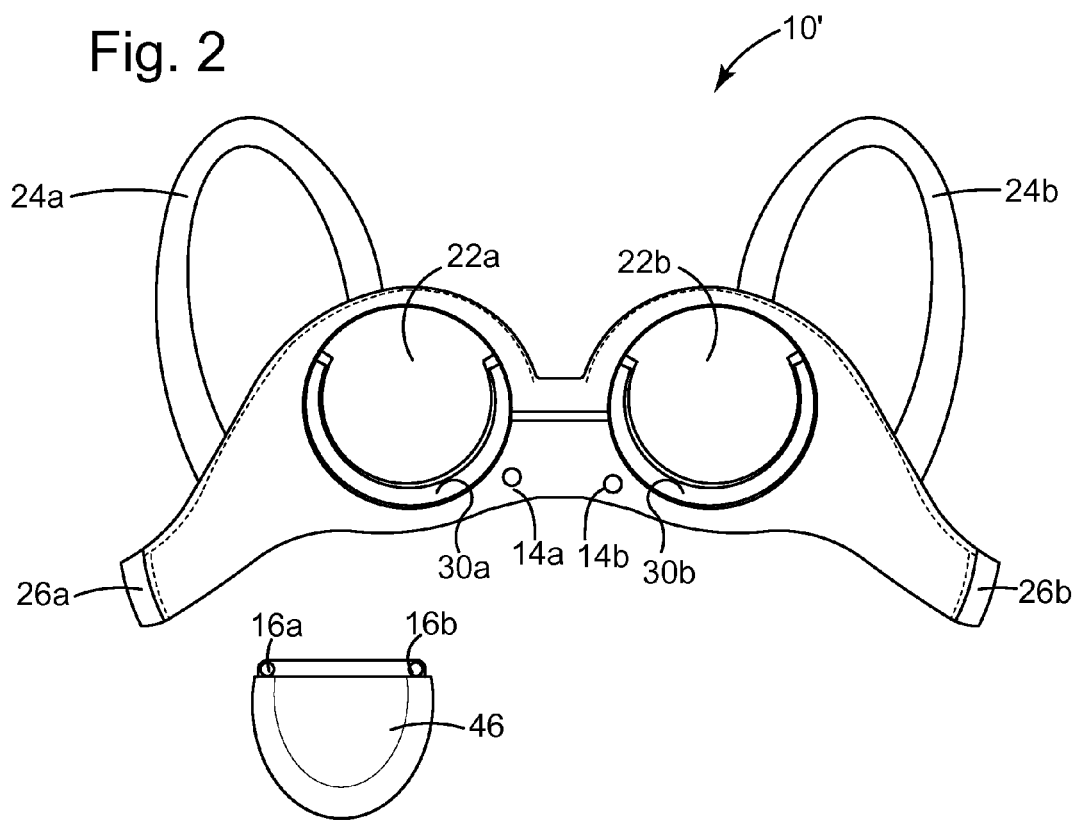
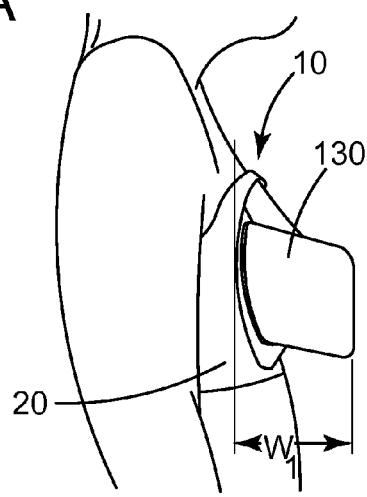

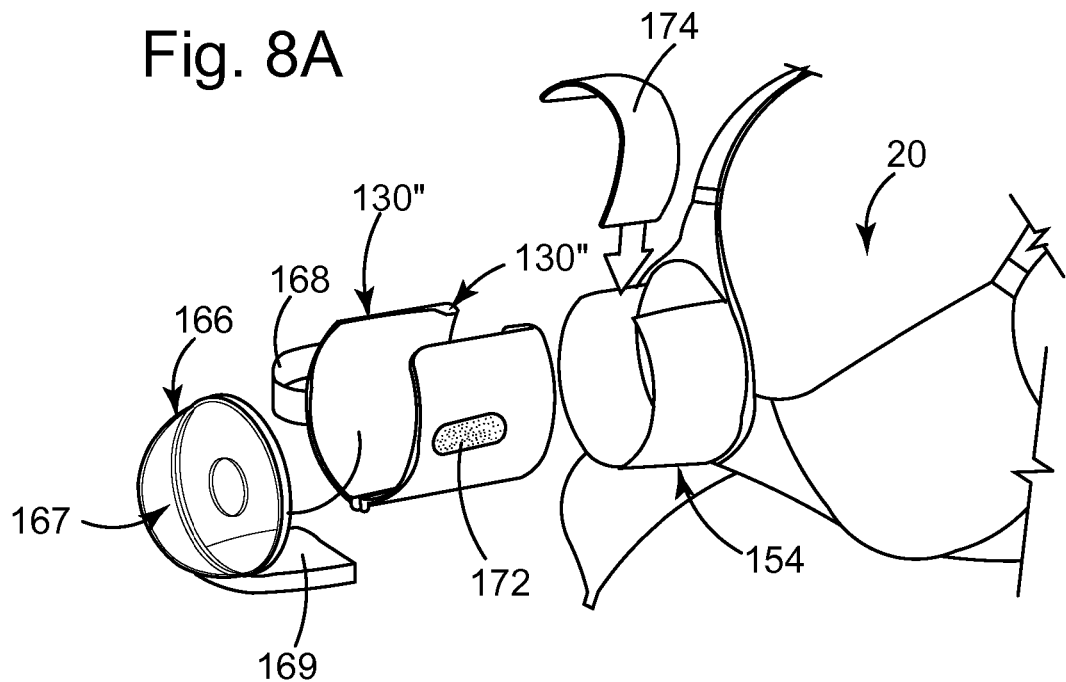
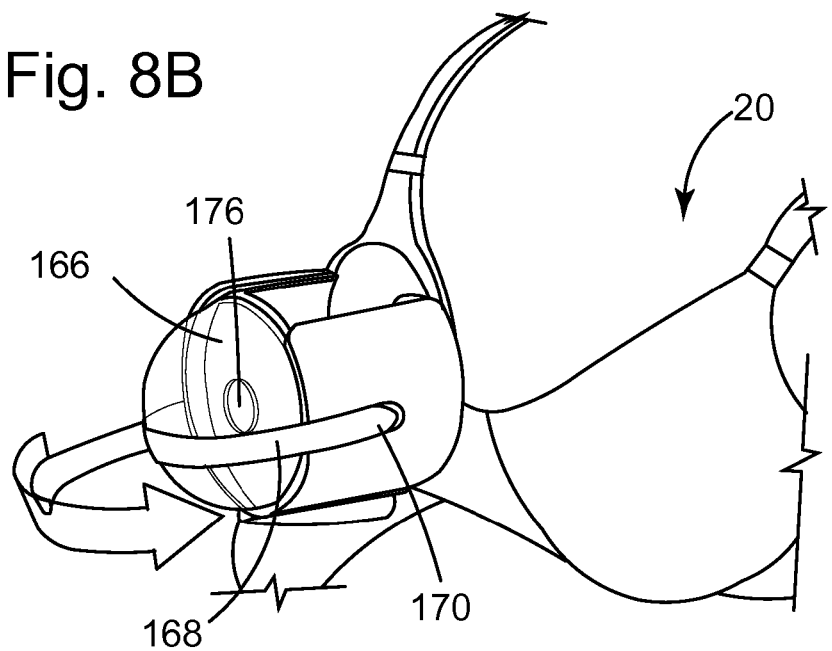

330

332

330

APPARATUS AND METHODS FOR COMPRESSING A WOMAN'S BREAST TO EXPRESS MILK IN A CONCEALABLE MANNER

CROSS-REFERENCE TO RELATED APPLICATIONS

This application claims priority to U.S. Provisional Application Nos. 61/838,220 and 61/838,223, filed on Jun. 21, 2013 and to U.S. Provisional Application No. 61/975,012 filed on Apr. 4, 2014, each of which is hereby incorporated herein by reference in its entirety.

FIELD

The present invention relates generally to breast pumps utilizing compression to enhance milk expression and that can be operated discreetly under clothing.

BACKGROUND

Conventional breast pumps are typically vacuum-powered to aid in breast milk collection. These pumps usually require a mother to be in isolation, fully engaged, and secured to a large vacuum pump for 30-minute sessions every 3 hours in order to express milk. Vacuum pumps can also reduce a woman's milk producing capabilities if adequate milk removal is not achieved. Many working mothers also feel guilty for taking breaks to pump, and cite that the most significant problems associated with this current methodology include lack of an adequate facility to pump, lack of time for pumping at work, and lack of time for cleaning pump equipment. Studies have shown that employment is a frequently cited barrier to breastfeeding, and working mothers experience a significantly shorter duration of breastfeeding than nonworking or part-time working mothers. Therefore, there is a growing societal and medical need for a method that allows working mothers to continue providing breast milk to their infant and there is a void for an effective and comfortable breast pump that allows a woman to discreetly collect milk.

The health benefits of breastfeeding for infants are extensive, including protection against diabetes, Crohn's disease, multiple sclerosis, allergic reactions, infections, and many other diseases; infants who breastfeed are 60% less likely to die from sudden infant death syndrome than infants who don t receive any breast milk. Therefore, the US government has issued a call to action, strongly urging that all infants be exclusively breastfed for the first six months of life, and drink breast milk through at least one year to achieve optimal growth, development and health. The Affordable Healthcare Act now mandates that breast pumps be covered by insurance companies to aid in preventive infant care. However, of the 4 million new births per year in the US, only 24% of infants are breastfeeding at 1 year and just 15% of infants exclusively breastfeed for 6 months.

Hand-expression is an alternative technique for breast milk collection that can be performed without the aid of conventional vacuum breast pumps or other pumping technologies. Compressing the breast milk glands in a rhythmic manner is known to produce milk secretion, but the manual procedure is not as efficient as electric vacuum-based pumps due to hand fatigue. In a recent study of mothers with full-term, poorly feeding infants, hand expression did not decrease the milk volume in post-partum women in comparison to electric vacuum-based pumping, suggesting that vacuum is not necessary to initiate and maintain maternal milk supply. Further, women who used hand expression were approximately 25% more likely to be breastfeeding 2 months post partum than women who used electric vacuum-based breast pumps.

Several patents exist which enable hands-free breast milk pumping (such as U.S. Pat. Nos. 6,227,936, 8,307,463, 6,213,840), but none include a compressing and/or heating feature for increasing milk expression. At least two patent applications present wearable breast milk expression systems and utilize air compression technology (such as U.S. Patent Application Publication Nos. 2005/0234370 and 2006/0106334). However, the present application includes several aspects which significantly improve upon the prior art.

Accordingly, there is a need for breast pumps that can enhance milk expression and can be operated by a woman discreetly under clothing.

SUMMARY OF THE INVENTION

Systems for expressing milk from a human breast are provided herein. In one embodiment, a system for expressing milk includes a brassiere configured to be worn by a user and having first and second openings formed therein, the first opening configured to receive a first breast and the second opening being configured to receive a second breast. The system can further include an initializing component positioned adjacent to at least one of the first and second openings and configured to apply pressure to a base of a breast, adjacent to a chest wall. The system can further include a clamping component configured to apply a pressure around a substantial area of a breast and being sized and shaped such that when a breast is disposed therein, the clamping component extends across an inferior portion of the breast.

The initializing component and the clamping component can vary in any number of ways. For example, the initializing component can be configured to apply pressure to a base of a breast, including a an inferior portion of a breast and first and second lateral sides, without applying pressure to a superior portion of the breast. In certain aspects, the initializing component includes a protrusion integrally formed along a first terminal end of the clamping component for positioning adjacent to a chest wall of a user. In other aspects, the initializing component includes an inflatable bladder configured to be disposed around a circumference of a base of a breast. The inflatable bladder can be encased in a housing having an outer surface that does not expand when the bladder is inflated. The clamping component can be configured to be manually adjusted by a user such that a user can control an amount of pressure applied to a breast during milk expression.

The compression mechanism can also vary in any number of ways. For example, the compression mechanism can include at least one inflatable bladder configured to extend around a circumference of a breast, the compression mechanism configured to apply cyclical or constant pressure along a portion of a breast.

The system can include a collection mechanism for collecting and transporting expressed milk to at least one containment mechanism that holds milk therein, the at least one containment mechanism being selectively detachable from the brassiere by a user. The collection mechanism can include a substantially leak-proof membrane configured to create a seal around the nipple and the areola. When the system is positioned on a user, the collection mechanism can be angled downward such that gravity facilitates milk collection into a one-way valve coupled to the at least one containment mechanism.

The system can further include a support member disposed along the first opening and configured to releasably couple to the clamping component such that the clamping component extends along an outer surface of the support member. The support member can include a pocket configured to receive a temperature-sensitive component configured to increase a temperature of a breast to facilitate milk output. In certain aspects, the containment mechanism can include a sensor configured to monitor a fill level to prevent overflow of milk from the containment mechanism.

Methods for expressing milk from a lactating human breast are provided herein and can include positioning an initializing component adjacent to a base of a breast, the initializing component applying a constant pressure to a breast, and adjusting a size of an expression component such that the expression component applies a pressure to superior and lateral surfaces of a breast, from an edge of an areola and to a region proximate to a base of a breast. The initializing component and the expression component can cause milk to be expressed from a breast.

The method can be performed in various ways. For example, the method can include activating the expression component after the initializing component is positioned on the breast, the expression component being at least one inflatable bladder. The method can include applying a vacuum to at least one of a nipple and an areola of the breast to facilitate expression of milk from the breast. In certain aspects, the initializing and expression components can be activated simultaneously, the initializing component applying a constant, non-cyclical pressure to the breast and the expression component applying a cyclical pressure to the breast. In other aspects, the initializing component applies a constant, non-cyclical pressure to the breast and the expression component applies a constant, non-cyclical pressure to the breast. After milk expression has begun and a size of a breast has decreased, a size of the expression component can be decreased so that the expression component applies an increased amount of pressure to a breast.

A method for retrofitting a conventional vacuum-based breast pump to improve milk output is also provided herein and can generally include positioning at least one compression component adjacent to a user's breast, a vacuum-based pump applying a vacuum to a nipple of the user's breast, and manually inflating the at least one compression component with fluid until the at least one compression component has a desired pressure, thereby increasing a flow rate and volume of expressed milk.

BRIEF DESCRIPTION OF THE DRAWINGS

The present invention will be more fully understood from the following detailed description taken in conjunction with the accompanying drawings, in which:

FIG. 2 is a perspective view of a brassiere having first and second openings for receiving a user's breast and first and second compression elements coupled thereto for applying pressure to a base of a breast to stimulate milk expression;

FIG. 3A is a side view of a brassiere having a clamping element attached thereto;

FIG. 8A is a perspective view of a milk expression system having a milk collection container, a detachable clamping component, and a brassiere;

FIG. 8B is a perspective view of the milk expression system having a milk collection container secured to the clamping component via straps;

DETAILED DESCRIPTION

Figure 1:
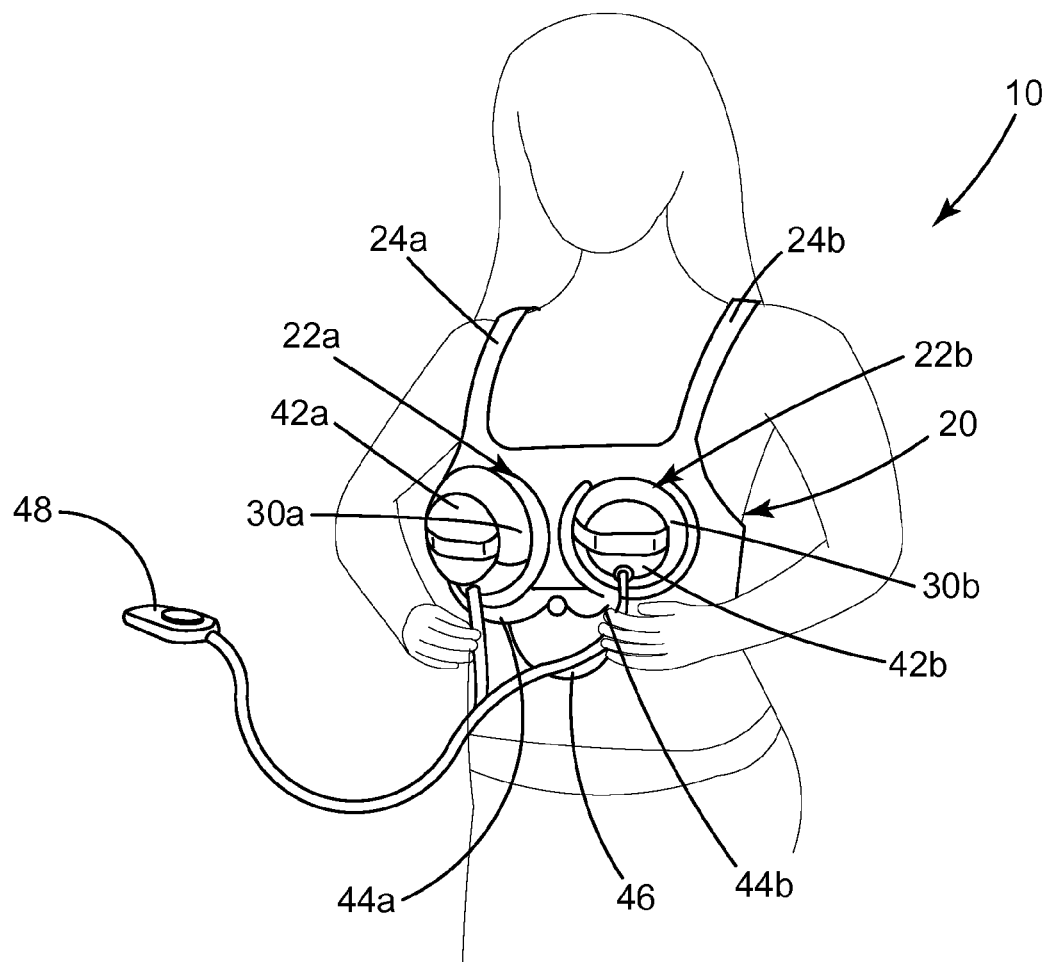
FIG. 1 is perspective view of an embodiment of a compression-based breast pump worn by a user in the form of a brassiere.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the scope of the invention and such dimensions are not intended to limit the types of shapes or dimensions that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Systems for expressing and storing breast milk are provided herein and generally improve upon manual techniques for expressing milk. The systems can be hands-free, concealable, and quiet so as to allow a woman to discreetly express milk in the presence of others. For example, the milk expression and storage system can be worn under one's bra or incorporated into a specialized bra. In this way, the system can be designed to be comfortably and discreetly worn under clothing for extended periods of time and the functional components may be engaged only when breast milk collection is desired. The milk expression components can be contained within a housing or privacy barrier so as to minimize visible movement of the system to others when the system is worn and activated by a user.

The systems herein improve upon manual techniques for expressing milk. For example, compression can be used to express milk, eliminating the need for bulky vacuum pumps and allowing the milk collection system to be contained in a compact and fully concealable system. In certain aspects, vacuum can be applied in conjunction with compression techniques, yielding higher milk output than systems that rely on vacuum without compression of the breast. In some embodiments, the system can include multiple components that apply a pressure to a breast. For example, a pressure-initialization component can optimize a mother's hormone release by compressing a base of a breast at a constant or cyclical pressure and one or more additional compression mechanisms can apply a pressure to a larger area of a breast, such as to inferior and lateral sides of a breast. The system can include various modular components that can be removed from the system to increase comfort levels of the user when the system is not activated and to allow for customized combinations of components.

An exemplary wearable system 10 for expressing and collecting milk is shown in FIG. 1. In the illustrated embodiment, the system 10 includes a wearable bra 20 resembling a nursing bra. The bra 20 can be custom made to incorporate one or more components of the systems herein or can be a standard nursing bra. In general, the bra 20 includes first and second openings 22a, 22b disposed therein, each opening 22a, 22b being configured to receive a single breast and having a substantially circular shape. The bra 20 can include first and second straps 24a, 24b that can be positioned over a user's shoulders and can be adjustable to provide support for a user's breasts. The custom bra 20 can have various components for expressing milk. For example, first and second initializing components 30a, 30b can be disposed along each of the openings 22a, 22b in the bra 20 and, as discussed in greater detail below, can apply pressure to a portion of a breast extending through the respective opening 22a, 22b. An initializing component 30 can be built into the base of the opening and/or can be detachable from the opening, but in either case, the initializing component 30 can apply pressure directly at the junction between a chest wall and a base of the breast. The system can further include at least one clamping/compression component (not shown) that massages or compresses a different portion of the breast than the initializing component 30a, 30b and facilitates milk expression. In some embodiments, the compression component can apply pressure to a larger area of a breast than the initializing component, such as an inferior portion and lateral sides of a breast. The custom bra can include padded breast cups (not shown) disposed around first and second openings to smooth out the appearance of the breast, as breast shape can be altered during milk expression. The breast cups can prevent appearance of leaks that often happens with lactating women. These padded cups may be fixedly incorporated into the bra or can be attached and detached from the bra at their discretion. The custom bra can include padded breast material that cover the breast and nipple (e.g., commonly known as the breast cup of a standard bra) disposed around first and second openings to smooth out the appearance of the breast, as breast shape can be altered by compression features during milk expression. The breast cups can prevent appearance of leaks that often happens with lactating women. These padded cups may be fixedly incorporated into the bra or can be attached and detached from the bra at their discretion or can be in the form of flaps of a standard nursing bra.

The bra 20 can include various components for collecting and transporting expressed milk. For example, first and second milk collection containers 42a, 42b can collect a user's expressed milk and can be coupled to the system 10 in various ways. The bra 20 can include various attachment mechanisms (not shown) for coupling to other components, such as an initializing component, housing, milk storage bag container and/or a controller that operates a pump. The milk collection containers 42a, 42b can be coupled to one or more tubes 44a, 44b for delivering milk to one or more milk storage containers (not shown). The bra 20 can include a holder or pocket for the milk storage containers/bags and/or a storage and clip area to attach the motor and pump components. In the illustrated embodiment, a single milk storage container is disposed in a pocket 46 on the bra 20, generally in between but below the first and second openings 22a, 22b. However, the milk storage container(s) can be positioned at various locations in the bra or on another portion of a user's body. A controller 48 can be electrically coupled to a pump (not shown) so that activation of the controller 48 delivers air or other types of fluid to the initializing components 30a, 30b and/or compressing components via one or more tubes 45a, 45b. This can cause various components of the system that receive the fluid to compress against a user's breast, causing milk expression. Alternatively or additionally, a manual actuator (not shown), such as a bulb, can be squeezed or otherwise depressed and can deliver air or other types of fluid to the initializing component and/or compressing components via one or more tubes. This can cause the components of the system that receive the fluid to compress against a breast. This manual actuator can be built into the bra, such as being fixed onto the bra straps or in the space in between the breasts for easy access by the user. In other aspects, the manual actuator can be detachable by a user.

FIG. 2 illustrates the exemplary custom bra 20 having first and second openings 22a, 22b, each for receiving a breast, and first and second initializing components 30a, 30b disposed thereon. The first and second openings 22a, 22b can be substantially circular shaped so that each opening can receive a breast. The openings 22a, 22b can be shaped in other ways, such as elliptical, square, rectangular, etc. A size of the openings 22a, 22b can be selected to accommodate a range of breast sizes (e.g., large breasts can have larger openings) and the openings 22a, 22b can be lined with elastic material to accommodate an even large range of breast sizes. A diameter of the first and second circular openings 22a, 22b can vary, but can be in the range of about 3 inches to 10 inches.

The initializing components, also referred to herein as pressure initializing components, promote hormonal release and increases milk expression by applying pressure to a base of a breast, i.e. at a location of a breast closest to a user's chest. In general, the pressure initialization component can be any mechanism that increases and decreases in size and partially or completely surrounds a base of a breast. The pressure initializing component can also generally help position a nipple so that it is aligned with a milk collection piece. The initializing components can have various sizes, shapes, and configurations. As shown in FIG. 2, the initializing components 30a, 30b can be substantially U-shaped such that the initializing components 30a, 30b do not apply a pressure to a top portion of a breast. As shown, the first and second initializing components 30a, 30b can be positioned around the first and second openings 22a, 22b, respectively, so that the initializing components 30a, 30b support a base of the breast. The initialization components 30a, 30b can be attached to the bra 20 in various ways. For example, the initialization component 30a, 30b can be located at the base of the breast, either as an insertable component that can be readily removed by a user or can be built into and fixedly attached to the bra and not intended to be removed by a user. The width of the initializing component 30a, 30b in a direction perpendicular to a surface can vary, but can be in the range of about 0.25 inches to 3 inches. These ranges can also vary depending on a size of a breast, as large breasts can have a wider initializing component and smaller breasts can have a smaller initializing component. The bra shown in FIG. 2 can include various components for supporting a user's breasts and facilitating comfort. This includes any of the features in FIG. 1, such as first and second straps 24a, 24b that can be positioned over a user's shoulders. The bra can further include first and second closure mechanisms 26a, 26b that can be mated together and located on a user's back and the closure mechanisms can be include Velcro, clasps, etc. A pocket 46 can be detachable from the bra 20 via first and second attachment mechanisms 14a, 14b for coupling the pocket 46 to an area in between the first and second openings 22a, 22b, adjacent to a user's sternum. These first and second attachment mechanisms 14a, 14b can mate with corresponding first and second attachment mechanisms 16a, 16b disposed on the pocket 46. As will be described in further detail below, this pocket can contain various components of the system, such as a milk collection container and/or a controller.

Figure 3B:
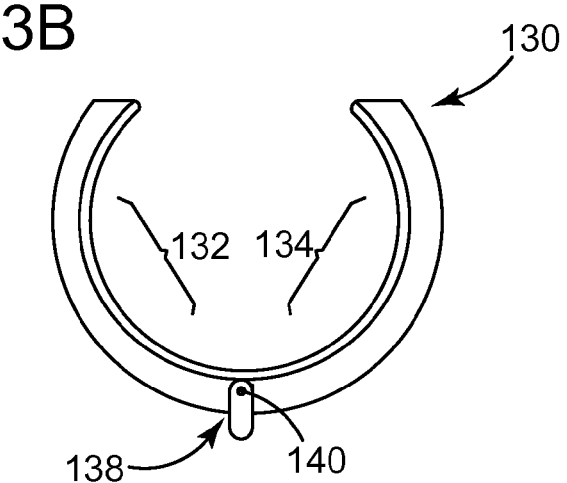
FIG. 3B is an end view of the clamping element of FIG. 3A.
Figure 3C:
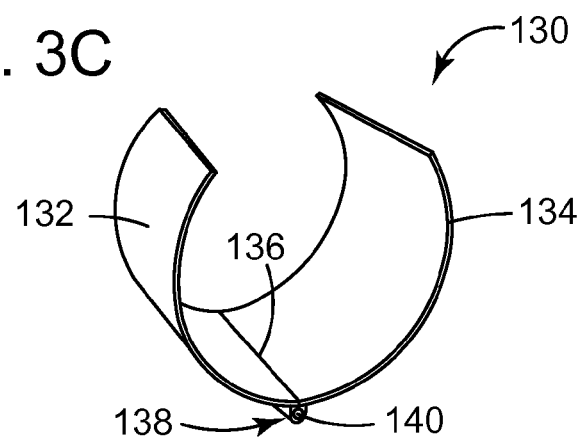
FIG. 3C is a perspective view of the clamping element of FIG. 3A in a resting configuration and detached from the brassiere.
Figure 3D:
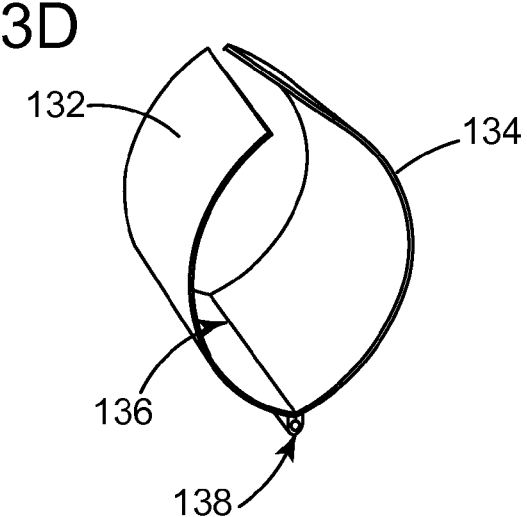
FIG. 3D is a perspective view of the clamping element of FIG. 3C in an compressed configuration.

FIGS. 3A-3C illustrate an embodiment of an initializing component that is referred to herein as a clamping component 130. As shown in FIG. 3A, the clamping component 130 can be sized and shaped to protrude out of the bra 20 to support the breasts and apply pressure thereto. The clamping component 130 can have a width $W_1$ in a direction generally perpendicular to a user's chest. The width $W_1$ can vary based on a cup size of a user's breast, but can be in the range of about 0.5 to 10 inches, preferably 0.5 to 3 inches. The clamping component 130 can have various sizes, shapes, and configurations. For example, the clamp can be adjustable in a direction perpendicular to a chest wall and can be adjustable in a direction substantially parallel to a chest wall such that an area of contact between the clamp on the inferior portion and lateral sides of a breast can be varied. For example, the clamp can include one or more telescoping features (not shown) that are expandable and collapsible. The clamping component can have various cross-sectional shapes. As shown in FIG. 3B, the clamping component 130 can have a U-shaped cross-sectional shape. The clamping component 130 can be shaped in various ways, for example, an open C-shaped cross-sectional shaped clamp that will remain open along a superior portion of breast, or a closed shape that extends around an entire circumference of a breast (i.e. along inferior, superior, and lateral surfaces), for example, a square, rectangular, circular, elliptical, triangular, tear drop, oval, cross-sectional shaped clamp. In the illustrated embodiment, the clamping component 130 can include a first curved portion 132 and a second curved portion 134 that form the U-shaped cross-section and can be separated by a hinge 136 such that the curved portions can pivot toward and away from one another about the hinge 136. This pivoting action can apply pressure to the user's breast. That is, when the curved portions 132, 134 are pivoted toward one another there is an increased pressure applied than when the curved portions 132, 134 are pivoted away from one another. The clamping component 130 can have a first, resting configuration as shown in FIG. 3C where the first and second portions 132, 134 are disposed at a maximum distance apart. The clamping component 130 can include any number of features, such as ratcheting, springs, etc. that can hold the clamping component 130 in a pivoted position, compressed configuration, as in FIG. 3D, so that a constant pressure is applied to a breast rather than a cyclical pressure. In this way, no rhythmic motion would be visible to others when the system is expressing milk. The clamping component 130 can be formed from various materials, but is preferably substantially rigid so as to clamp around a user's breast. Exemplary materials that can form the clamping component include inelastic materials such as plastic, metal, or hardened rubber. The clamping component can be integrally formed in the bra or can be selectively detachable therefrom in various ways, such as via Velcro, snaps, press-fit, interference-fit, etc. In certain aspects, the clamping component 130 can have a mating feature 138 disposed thereon for connecting to a correspondence mating feature (not shown) on the bra 20. As shown in FIGS. 3B-3C, the mating feature 138 on the clamping component 130 can include a protrusion extending axially along an outer surface thereof, below the hinge 136 and having an opening 140 configured to receive a corresponding protrusion on the bra.

Figure 4A:
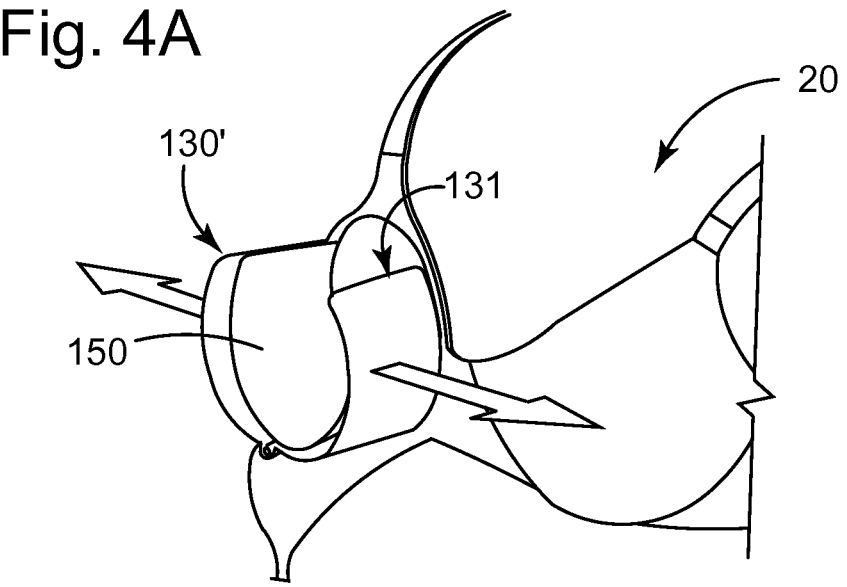
FIG. 4A is a perspective view of the clamping element of FIGS. 3A-3D having a compression bladder disposed thereon in a resting configuration.
Figure 4B:
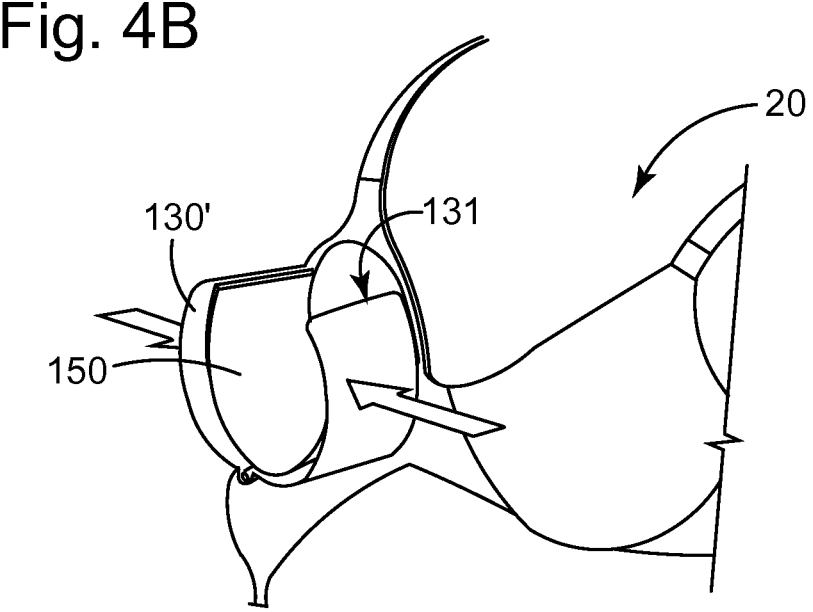
FIG. 4B is the compression element of the compression element of FIGS. 3A-3D having a compression bladder in a compressed configuration.

The clamping component can include any number of additional features. For example, the clamping component can be used with one or more compression components, e.g. compression bladders. In one embodiment, the clamping component can include one or more bladders coupled thereto that can be inflated to a given volume and pressure. The clamping component can serve an additional purpose of preventing outward deflection of one or more optional inflatable bladders by further compressing the breast with a cyclical pressure or an adjustable, constant pressure. The bladder(s) can extend along a substantial portion of an inner surface of the clamping component or can be positioned at any axial location of the clamping component. The clamping component can be used to increase contact between the one or more compression bladders and a breast and can help user control a magnitude and location of pressure applied to a breast. FIGS. 4A-4B illustrate a clamping component 130' coupled to a bra 20 and having a single inflatable bladder 150 moving between resting and compressed configurations. The clamp 130' can include a ramped or angled side-profile when the clamp 130' is coupled to a bra 20, as in FIG. 3A, and this can cause one or more inflatable bladders 150 to apply a force at an angle (e.g., at a 0-45° angle relative to the breast as opposed to 90° directly toward the breast if 0° is a force at the intersection of the chest wall and breast faces towards of back of the body) so that the breast is pushed away from a chest wall. A compression force that acts directly on a breast, particularly in the sloped area near a nipple, can force the breast inward toward a user's chest wall and this can complicate milk collection. This clamp 130' can also be designed as a wedge insert inside the bra 20 or underneath the bladder 150. Any angled design can help to compress the breast slightly away from a chest wall instead of directly on the breast, which at highly sloped portions, e.g., close (less than an inch) to the areola, compresses the breast towards the body. As will be appreciated by those skilled in the art, the clamping component 130' can have any or all of the features of the clamping component of FIGS. 3A-3C. As shown in FIG. 4A, when the clamping component 130' is in the resting configuration, the bladder 150 is deflated and does not include fluid therein. As shown in FIG. 4B, when the clamping component 130' is in a compressed configuration, the bladder 150 is inflated and applies a compressing force against a base of a user's breasts without compressing a top portion of a breast. A top portion of the breast that is not compressed by the clamping component 130' and not compressed by the bladder 150 can be in the range of about 0-15% of a total surface area of the breast. Preferably, the clamping component 130' can be substantially rigid and can act as a privacy barrier that limits movement visible to others when the bladder 150 is being inflated or deflated.

Figure 4C:
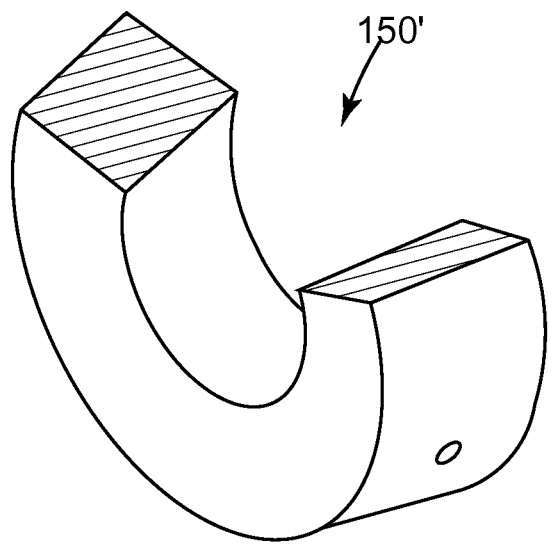
FIG. 4C is perspective view of yet another exemplary compression bladder being substantially U-shaped and having an increased width for compressing a larger portion of a breast.
Figure 4D:
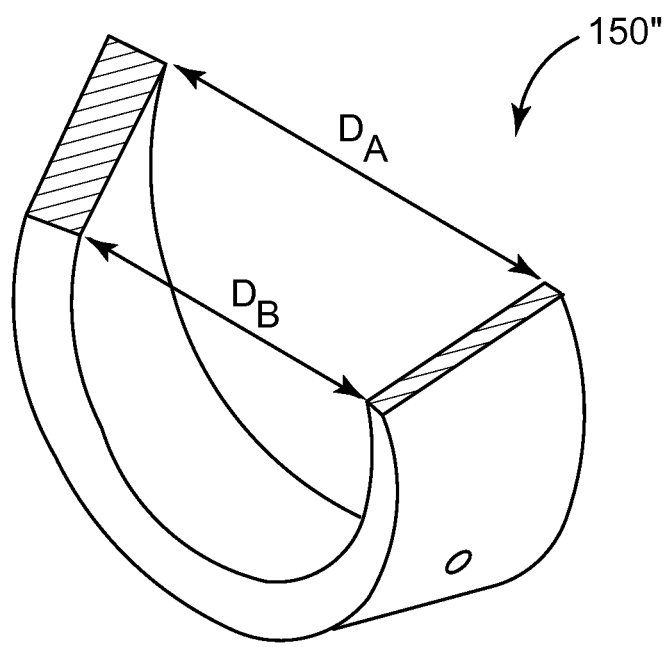
FIG. 4D is a perspective view of yet another exemplary bladder element having a tapered profile.

The inflatable, compression bladder(s) in the clamping component 130' can have various sizes, shapes, and configurations. The inflatable bladder 150 can be substantially flexible and can be formed from various materials, such as rubber, neoprene, latex, or PVC. The inflatable bladder 150 can have a maximum inflation volume in the range of about 0.5 inches to 5 inches and a pressure in the range of about 0.5 psi to 10 psi. FIGS. 4C and 4D illustrate two exemplary inflatable bladders 150', 150" having various widths and cross-sectional shapes. A wider bladder 150' as in FIG. 4C can be beneficial to create more pressure along more surface area of a breast and a thinner bladder 150" as in FIG. 4D can be useful to localize pressure in specified areas, e.g., just along a base of a breast or just at an areola. In general, thinner bladders can also be beneficial from a sizing and manufacturing perspective because multiple bladders can be connected together to accommodate adequate pressure around a large breast, while one bladder can be sufficient for a small breast. The bladder 150' can have a uniform width and a semi-circular shape while the bladder 150" can have a semi-circular shape that varies along its width. That is, the bladder 150" can have a first inner diameter $D_A$ positioned on a side toward a chest wall and a second diameter $D_B$ positioned on a side away from a chest wall, the first diameter $D_A$ being greater than the second diameter $D_B$. In general, the bladder(s) can be positioned at various angles on a breast, such as axially aligned with a chest wall or angled relative to a chest wall.

Along with an initializing component, a milk expression system herein can further include a breast-compressing component. The breast-compressing component can include one or more compression mechanisms, e.g. inflatable bladders, which stimulate milk expression from the breast. The use of an initializing/clamping component and compression mechanisms can cause an increase in milk output compared to the use of an initializing component or a compression mechanism alone. A compression mechanism can include one or more inflatable bladders that can be positioned around a substantial portion or entire circumference of each breast and can be oriented parallel to a chest wall. The bladders can overlap the entire circumference of the breast to accommodate a range of breast sizes, with large breasts having minimal overlap while small breasts having substantial overlap. The one or more inflatable bladders can have various sizes, shapes, and configurations. For example, the bladders can be truncated, cone shaped, tapered, etc. to adapt to the slope of the breast or can be substantially U-shaped, allowing for size adjustment and preventing the bladder from applying pressure to the highly sloped top portion of a breast. The inflatable bladders can be substantially flexible and can be formed from various materials, such as neoprene, rubber, latex, polyurethane, polypropylene, PVC or any other FDA approved flexible material. The inflatable bladders can have a maximum inflation depth deflection in the range of about 0.5 to 5 inches and a pressure in the range of about 0.5 psi to 10 psi. The system can include any number of bladders per breast, such as two, three, four, or more bladders. In use, one or more of the bladders can be inflated and deflated with air or another fluid or gas in a rhythmic manner to stimulate milk expression. The bladders can be made of any such impermeable material such as natural rubber or synthetic material that can withstand the generated pressure. The bladders can also be made from material that is resistant to mold, mildew, bacteria, and is generally suitable for machine washing in a dishwasher or in a clothes washing machine. The bladders themselves can be fixedly attached to a bra via Velcro, buttons or magnets or inserted into a bra via a sleeve or other holding mechanism in order to be properly placed around breast. The bladders can compress all or some quadrants of the breast that contain milk ducts, including the base of the breast to the nipple. Each bladder can have one or more port, located anywhere on the bladder for compressed air to enter/exit therethrough.

The clamping component can have various features for applying compression to particular regions of a breast, including an initializing component for applying additional compression to a base of a breast. This is shown, for example, in FIGS. 4A and 4B as a protrusion 131 that primes or initializes the breast. This protrusion 131 can extend uniformly along a first terminal end 133 of the clamping component 130' such that lateral and inferior portions of the breast are compressed uniformly as a result of a size of the protrusion 131. The clamping component 130' can have features that facilitate comfort. A sleeve or liner made of foam or other soft material (not shown) can be positioned along inner surfaces of the clamp, the initializing component, and/or the bladders to improve comfort.

Figure 5:
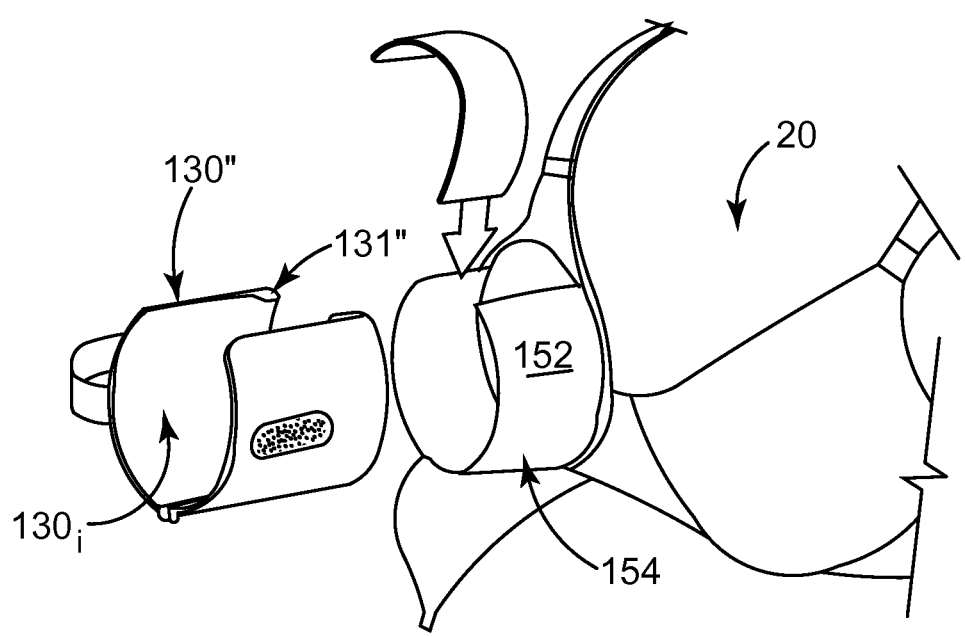
FIG. 5 is an exploded view of a milk expression system that generally includes a brassiere and a detachable clamping element.

The components of an expression system can be joined together in various ways and can be modular to facilitate removal, cleaning, and reattachment of the components in the system. FIG. 5 illustrates an embodiment of an expression system that includes a removable U-shaped clamping component 130" that can be disposed along an outer surface 152 of a U-shaped support structure 154. As shown, the U-shaped clamping component 130" can be removable from the support structure 154, the support structure 154 being fixedly attached to the bra 20 as the support structure 154 is not intended to be removed by a user. The clamping component 130" can include an initializing component 131" integrally formed thereon for creating a baseline, constant compression against a base and lateral sides of a breast and not a top portion of a breast. As in the embodiment in FIG. 4A, the clamping component 130" can include one or more compression components (not shown), such as one or more inflatable bladders, spaced at various locations along an inner surface 130i of the clamping component 130". As in the previous embodiments, a sleeve or liner made of foam or other soft material can be positioned along inner surfaces of the clamp, the initializing component, and/or the bladders to improve comfort.

Figure 6A:
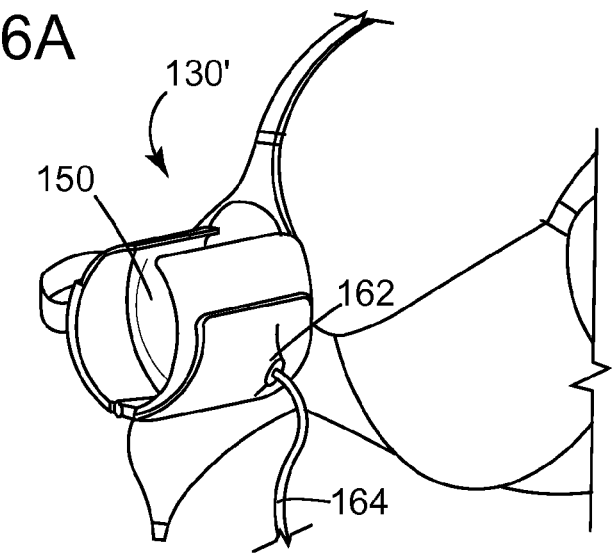
FIG. 6A is a perspective view of the compression element of FIGS. 3A-3D having a tube for delivering fluid thereto.
Figure 6B:
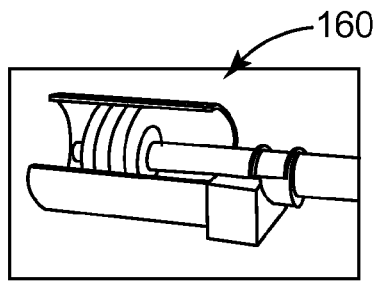
FIG. 6B is a perspective view of the hydraulic pump disposed external to the compression element.
Figure 7:
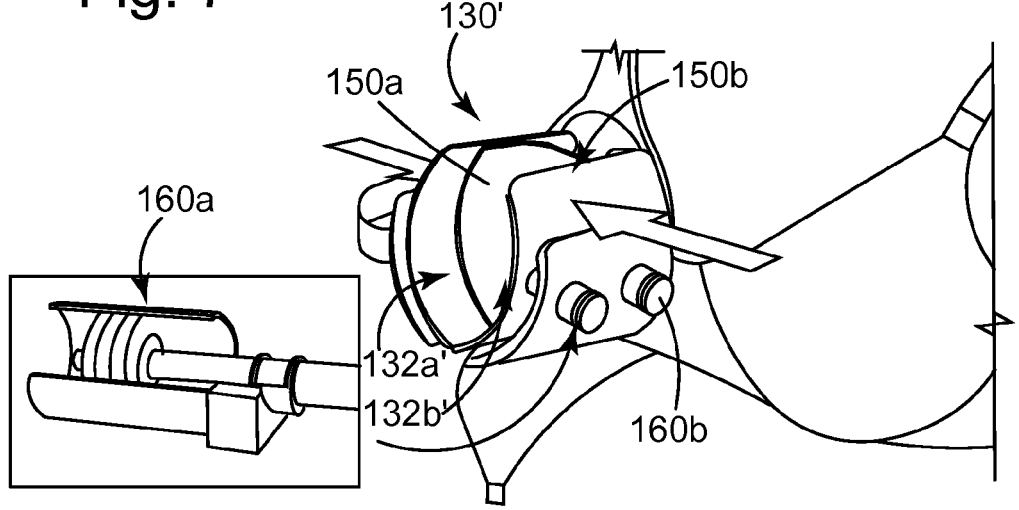
FIG. 7 is a perspective view of the compression element of FIGS. 3A-3D having a piston disposed therein for controlling expansion and compression of the compression element.

The compression components, i.e. inflatable bladders, can be expanded in various ways. For example, FIGS. 6A-6B illustrate a milk expression system that includes a hydraulic or pneumatic pump actuating a piston 160 to compress the breast. The piston 160 can be disposed external to the bra 20 and as shown in FIG. 6A, at least one tube 164 can connect the pump to the bladder 150 via a port 162. When the pump is activated, as described in greater detail below, the pump can force fluid, e.g. air, through the tube and into the bladder 150. This can cause the piston 160 to squeeze the clamping component 130' around a breast, applying a baseline pressure to the breast. The baseline pressure applied by the bladder 150 can be precisely controlled with the pneumatic piston 160. More specifically, the pneumatic piston 160 can drive air into the port 162, creating an initial compressing force prior on a breast to any cycling compression and expansion of the bladder 150. This can enable users to create initial compression to prime the breast for milk expression and to align the bladder with the breast tissue. As shown in FIG. 7, a milk expression system can include two pneumatic pistons 160a, 160b in fluid communication with a first compression component 150a disposed along the first curved portion of the clamping component 130' and a second compression component 150b disposed along the second curved portion of the clamping component 130'. In the illustrated embodiment, the compression components 150a, 150b are inflatable bladders. Alternatively, two inelastic C of J-shaped clamps may be used to create constant or cyclic compression on the breast, in place of or in addition to, inflatable bladders. In use, the one or more pistons 160a, 160b can transfer a small amount of air or liquid to the compressing components 150a, 150b to compress the breast independently or simultaneously to compress the breast from both sides. For example, a first hydraulic or pneumatic piston 160a can cycle at a user-defined frequency and can transfer a small amount of air or liquid to displace the left clamp 132a' and compress the breast. A second hydraulic or pneumatic piston 160b can transfer a small amount of air or liquid to displace the right clamp 132b' to compress the breast from both sides. Alternatively, the first side 132a' of the clamp can remain stationary, while the second side 132b' of the clamp 130' can move toward the first side to create compression. In another embodiment, vacuum could be used to cycle a small amount of air if air was initially fed into the system to manually to squeeze the breast, and then the vacuum could be used to cycle the compression of the bladders 150a, 150b. In this example, removing air from the bladder would release pressure and displacing the same air back into the bladder would cycle the compression on the breasts. Alternatively, a tube (not shown) can extend under the clamp 130' that connects the two sides so that a little more air or liquid can push a small cylinder on each side of the breast to compress the breast. This can enable compression applied by the bladder to be precisely controlled with a small amount of liquid or air, enabling the use of a low flow rate motor that would have significantly quieter operation. Further, different sized clamps could be available to users of a range of sizes. As will be appreciated by those skilled in the art, any number of pumps/pistons can be used and can be in fluid communication with any number of bladders for initializing and/or compressing a breast.

The inflatable bladders can be expanded in other ways, such as using a manual pump that does not require electrical powering. For example, a manual pump feature (not shown), such as an inflation bulb, can allow a user to inflate the bladders to an optimal pressure and can hold that pressure in the bladders constant. When a user feels more pressure is needed, the user can manually inflate the bladders again to add more compression (i.e., this may occur as the breasts empty). In this embodiment, inflation and deflation could be accomplished more silently and with less bulky components without a need for a wearable motor. Less cyclic motion can also improve the discreet appearance of the device and reduce motion that could complicate milk collection.

A clamping component can be attached to a bra in various ways. FIGS. 8A-8B illustrate the clamping component 130" of FIG. 5 and the U-shaped support structure or sleeve 154 in more detail, along with a milk collection container 166. The support structure/sleeve 154 can receive an inflatable bladder (not shown) or heating component (not shown) that can pre-warm breasts prior to pumping to improve milk output. The support structure 154 can be made from soft fabric, such as cotton, spandex, or will to improve comfort, as a user can chose to wear the support structure for longer periods of time than the other detachable components. As shown, the U-shaped clamping component 130" can be removable from the support structure 154, the support structure 154 being fixedly attached to the bra 20 as the support structure 154 is not intended to be removed by a user. In this embodiment, the clamping component 130" can include the initializing component 131" integrally formed thereon can be for creating a baseline, constant compression against a base of a breast and not a top portion of a breast. Alternatively, the clamping component 130" (and accompanying initializing component, if present) can be sized and shaped to compress around an entire circumference of a breast. The clamping component 130" can have various attachment mechanisms for coupling the clamping component 130" to the milk collection container 166, such as at least one strap 168 that extends around an outer surface 167 of the container 166, generally across a rounded outer surface of the milk collection container, the strap 168 having a terminal end 170 with Velcro that attaches to corresponding Velcro 172 on an outer surface of the clamping component 130" to secure the milk collection container 166 to the bra 20. An extension portion 169 can be formed on the milk collection container 166 for mating with an inferior surface of the clamp 130", such as the protrusion 138 and/or the opening 140 thereon to provide further support. As shown, the system can further include a strap 174 that can extend around a top open portion of the support structure 154 and a top of a breast, and can help secure the clamping component 130" and the milk collection container 166 to the sleeve 154. When the components 154, 130", and 166 are coupled together, as in FIG. 8B, an opening 176 in the collection cap 166 can be flush with a terminal end of the clamping component 130" and a terminal end of the support structure 154 so as to minimize bulkiness of the system, the terminal ends being disposed on a terminal end at a furthest distance from a user's chest.

Figure 9A:
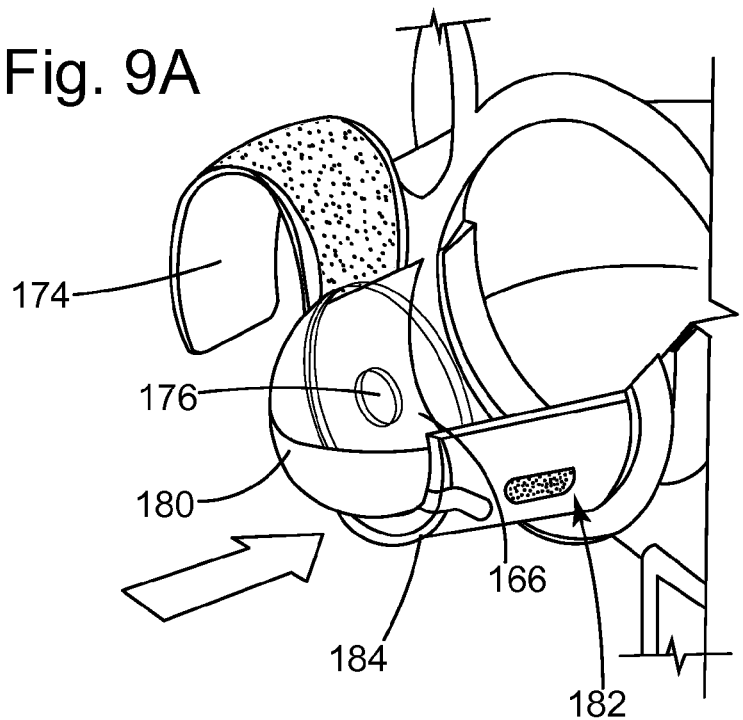
FIG. 9A is a perspective view of a milk expression system having a cover for holding a milk container in contact with a user's breast and in contact with other components.
Figure 9B:
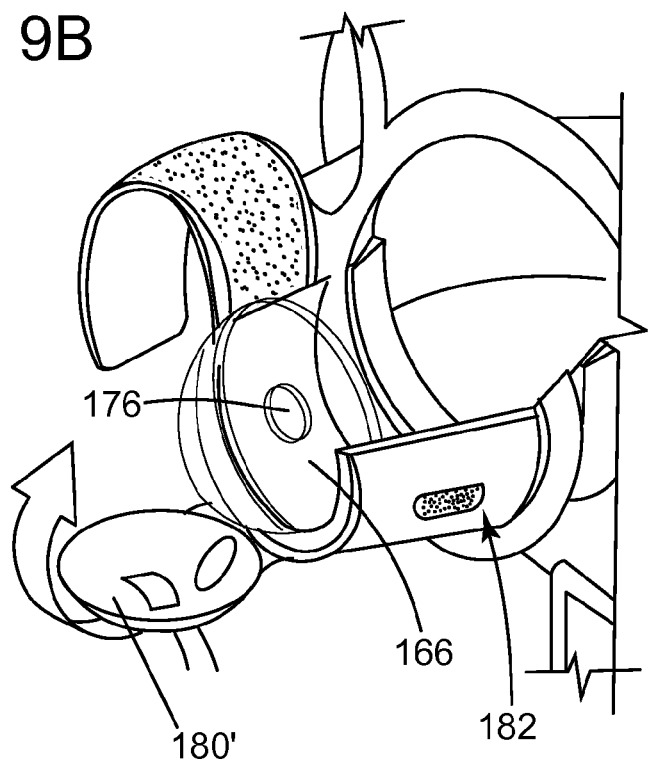
FIG. 9B is a perspective view of the milk expression system of FIG. 9A having a detachable cover for securing the milk container to other components.

FIGS. 9A and 9B illustrate other mechanisms for holding a milk collection container in place during milk expression. FIG. 9A illustrates a holder 180 that can receive the milk collection container 166. The holder 180 can be elastic and/or flexible so that the holder 180 can stretch to accommodate the milk collection container 160. The holder 180 can be formed from various materials, such as elastic fabric. The holder 180 can have various sizes, shapes, and configurations, but can have a surface area that is at least 20% of an outer surface of the milk collection container 166 so that the holder 180 can hold the container 166 so that the opening 176 in the container 166 is adjacent to and flush with the clamping component/housing. FIG. 9B illustrates a holder 180' in the form of a cap having substantially the same size and shape as the hemi-spherical portion of the collection container 166. As shown, the cap 180' can be used with a Velcro strap to secure the milk collection piece in place. These holding mechanisms can be used with any of the clamping components previously described, or can be used with a housing 182 shown in FIGS. 9A and 9B. The housing 182 can have a ribbed portion 184 extending around a circumference of a terminal end thereof, the ribbed portion 184 for holding the collection cap 166 being adjustable. More specifically, the ribbed portion 184 can have a plurality of folds so that the ribbed portion 184 can be stretched, increasing a length of the housing 182 in a direction perpendicular to a chest wall of a user, and compressed toward a user's chest well, decreasing the length of the housing 182. In this way, the connection between the housing 182 and the collection container 166 can help accommodate a range of breast lengths. Each of the housings can include an additional attachment mechanism that can help secure the milk collection container in place, such as the strap 174 that extends around a top portion of a breast.

Figure 10A:
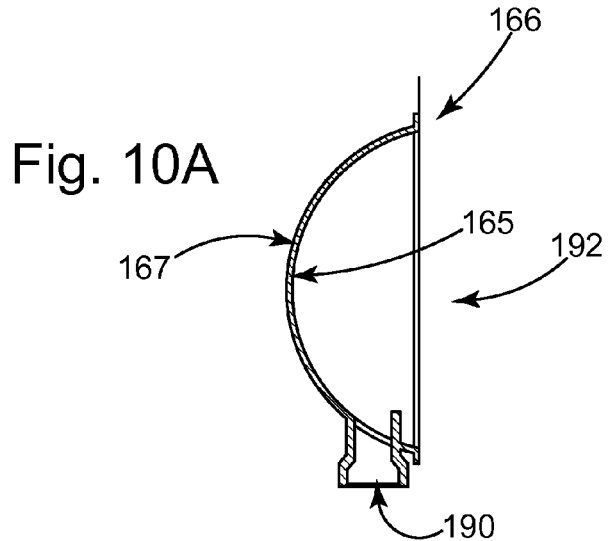
FIG. 10A is a side view of an exemplary milk collection container.
Figure 10B:
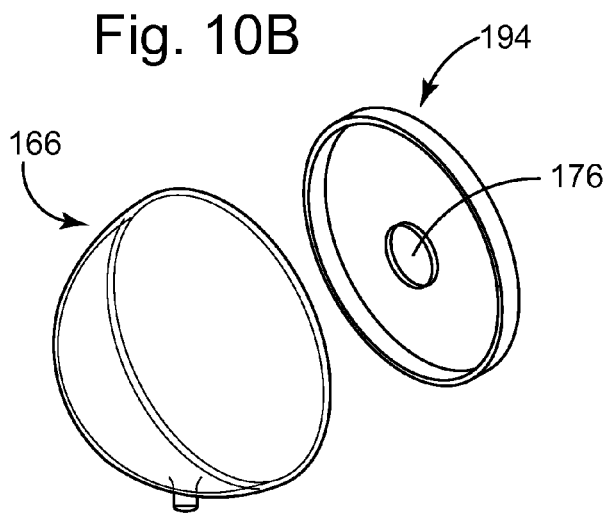
FIG. 10B is an exploded view of the milk container of FIG. 10A and a removable cover for receiving a nipple therethrough.

A milk expression system can include various components for collecting and holding expressed milk and optionally transporting expressed milk into another container external to the system. In general, milk-collecting and milk-transporting components can be made of inexpensive materials, such as polypropylene or other FDA approved, BPA fee plastics, so that the simple piece may be replaced with every session, eliminating the need for cleaning. These pieces can be dishwasher-safe to promote easy cleaning and reusability. A collection mechanism can have various sizes, shapes, and configurations. FIG. 10A illustrates the milk collection mechanism configured to hold and/or transport milk as it is expressed from a user's breast. In the illustrated embodiment, the collection mechanism includes a substantially hemi-spherically shaped cap 166 having a circular opening 192. A highly sloped, curved inner surface 165 of the collection mechanism 166 can be coated with a nonstick material to encourage flow of milk downward. The collection mechanism 166 can itself serve as a storage container for holding the expressed milk or the collection mechanism can include one or more features for transporting expressed milk to another storage vessel. As shown in FIG. 10A, the collection cap 166 can include one or more ports formed therein that can be coupled to a tube (not shown) that transports the expressed milk to a holding mechanism. A single port 190 can be formed adjacent to the opening 192 in the collection cap and can be oriented so that milk collected through the opening will flow toward the port 190 due to gravity. As shown in FIG. 10B, a flexible cover or membrane 194 can be sized, shaped, and configured to connect to the milk collection cap 166 and can receive a nipple in the hole 176 therethrough. The flexible membrane 194 can have a substantially circular cross-sectional shape sized to correspond to the circular opening 192 in the milk collection cap 166. An expandable/collapsible soft goods material (not shown) can be located at the end of bladder housing material, i.e., the end closest to the nipple, so that the user can adjust the placement of the collection cap to accommodate a snug fit. The flexible membrane 194 can be designed for a snug fit such that when the nipple is inserted through the substantially circular opening 176 formed in a center of the membrane 194, the flexible membrane 194 prevents leak or milk accumulation outside of the milk collection cap 166. When a nipple is extending through the circular opening 176 and into the milk collection cap 166, the flexible membrane 194 applies pressure in the range of about 0.5-2 inches behind the nipple and secures the nipple in place. The opening 176 can be shaped in other ways, such as a tear-drop, ovular, and elliptical, square, rectangular, or triangular. The opening 176 can be sized to accommodate various nipples, but the circular opening can be in the range of about 0.5 to 3 inches in diameter. The opening 192 in the milk collection cap 166 can have substantially the same diameter as an outer diameter of the flexible membrane 192 or can be slightly smaller than the outer diameter of the flexible membrane 192. In general, the outer diameter of the flexible membrane 194 can be in the range of about 1 to 8 inches.

Figure 10C:
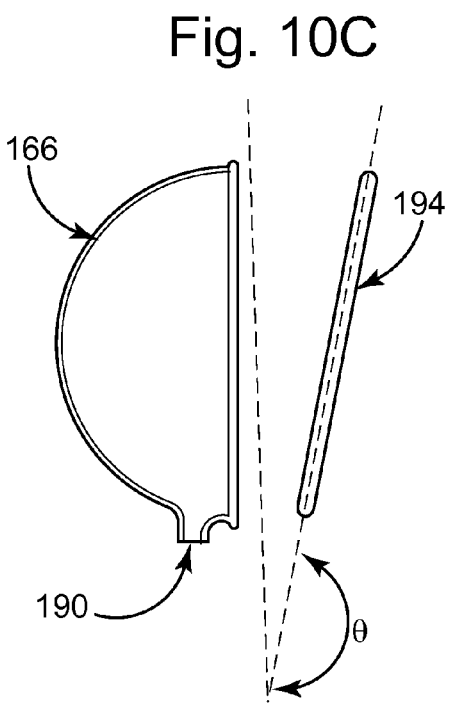
FIG. 10C is an exploded view of the milk container and removable cover of FIG. 10B, the removable cover being disposed at an angle relative to the milk container that can help prevent leaks.

The milk collection cap and the flexible membrane can be coupled together in various ways, such as via a strap, compression fit, snap fit, or any other attachment mechanism known in the art. The collection cap and the flexible membrane can be manually attached and detached by a user to facilitate cleaning and replacement of parts and to allow a user to omit the flexible membrane from the collection mechanism. As shown in FIG. 10C, the flexible membrane 194 can be angled in the range of about 90° and 135°, the angle θ being measured from a bottom portion of the milk collection container 166 to a top portion of the flexible membrane 194 at the breast, to help to create a tighter seal beneath the nipple where milk is likely to spill. Similarly, the flexible membrane can be shaped to hug the breast to enable a tighter fit. To further prevent leaks, the collection cap 166 may be coupled with a simple constant vacuum mechanism to further pull the nipple into the collection cap 166 and create a tight seal. The flexible membrane 194 can be formed from various materials, such as silicone or any other flexible, FDA approved material which is machine or hand washable. The collection 166 can also be formed from various materials, such as polypropylene or other FDA approved, BPA free plastics which are machine or hand washable. The collection mechanism can have flexibility in the ability to collect milk, for example, having interchangeable pieces that either collect milk discreetly or can easily be substituted with a custom fit bottle or milk storage bag to accommodate a user's preference.

Figure 11A:
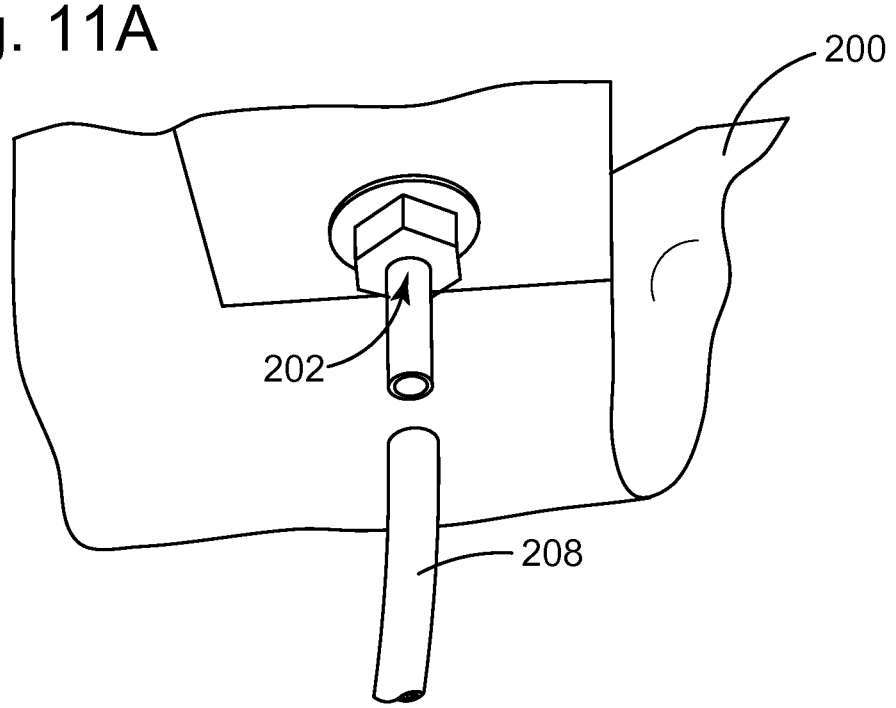
FIG. 11A is a perspective view of a collection bag and tube for coupling to a valve of a milk collection mechanism.
Figure 11B:
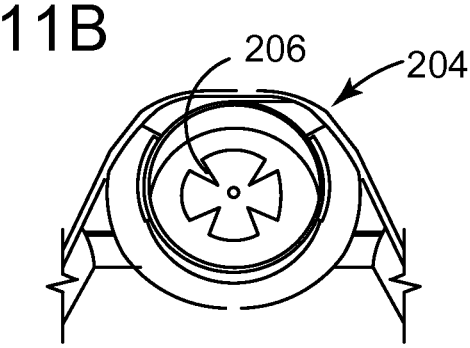
FIG. 11B is a perspective view of a valve that can receive the tube of the collection bag of FIG. 11A.

A milk expression system can include various storage containers or storage bags for holding expressed milk. A milk storage bag 200 is shown in FIG. 11A and is configured to detachably connect to the exit port/valve 190 of the milk collection cap 166. Different sized storage bags 200 can be made to accommodate various volumes of milk, in the range of about 4-12 ounces of milk. Bags 200 can be stored in a pocket located in the bra, such as the front pocket 46 shown in FIG. 2. The pocket (not shown) can be formed from leak-resistant material in order to prevent leaks of expressed milk. The milk storage container such as the bag 200 can be appropriately shaped to fit within the pocket and resist bulging, i.e. the container can have a size and shape that substantially corresponds to a pocket/pouch in the bra that holds the container therein. The container or storage bag 200 can have at least one port 202 formed therein, depending on the mechanisms of milk transport. In general, the ports can be sealed when not connected to the milk transport system, via any sealing mechanism known in the art, such as a one-way valve, a cap, a snap, etc. FIG. 11B illustrates a one-way valve sealing mechanism having a valve 204 with a flap or several leaflets 206 that open when a tube or port is inserted therethrough and that close upon removal of such tube or port. The valve 204 can be disposed in the port 202 of the storage bag 200. As shown in FIG. 11A, a tube 208 can be designed to fit snuggly into the valve (not shown) but a slightly small diameter hole is at the top of the valve opening to prevent the tubing from rising above the lowest level of the milk collection container. Otherwise, milk would not effectively collect into the container/storage bag. The milk collection cap can wrap underneath the breast, as shown in FIG. 8A, and can allow for the valve 204 to be located closer to the body in order to minimize kinking of the tubing, displacing the tubing, and/or minimize bulk. The nursing bra (not shown) can also be equipped with a small hole to allow the milk collection valve to be easily attached to the disposable collection bags the milk storage container. Where a collection mechanism includes a collection cap 166 and a milk storage bag/container 200, at least one of the ports can couple to a tube for transporting the milk between the collection cap and the milk storage container. The milk storage container 166 can be kept in proper place on the bra, e.g. between first and second openings, below first and second openings, etc., or on the user via attachment directly to the bra, directly to the compressing clamp or other inflatable bladder housing piece, or attachment to a leak-proof protective barrier. Attachment can be achieved through any attachment mechanism such as snaps, adhesive material, tied strings, clasp, etc.

The milk collection container can have any number of features that facilitate cleaning and ease of use. For example, a milk collection container or storage bag can have a resealable mechanism to retrieve the milk at a later date. A milk collection container or storage bag can have a spout that helps drain the milk into a bottle or other storage container. The milk collection mechanism can be lined with non-stick coating such as Teflon to prevent milk from sticking during pouring and to ease cleaning. The milk collection container can also be designed to have an easy-pour spout for milk removal. The milk collection container or storage bag can incorporate a level sensor (not shown) that indicates when the milk has reached a safe level prior to overflowing.

Figure 12A:
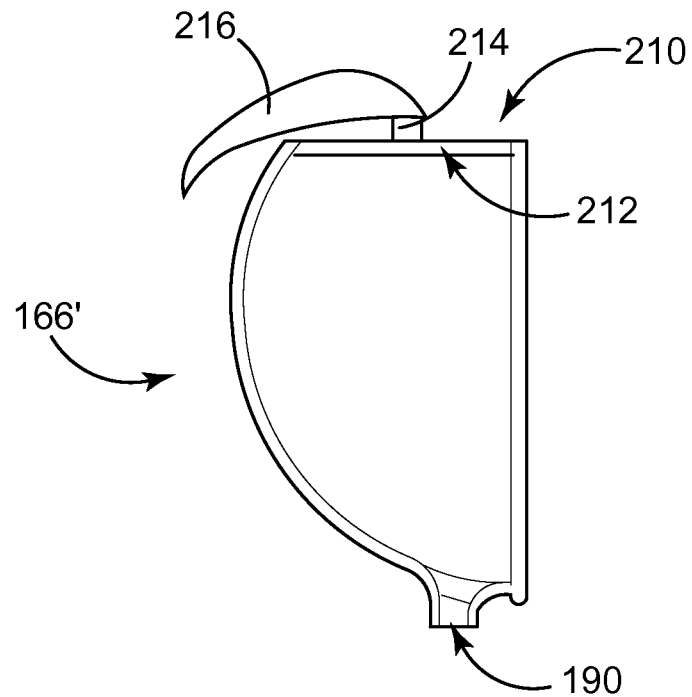
FIG. 12A is a side view of a milk container having an expandable portion that can be selectively expanded by a user via a handle in order to apply a vacuum.
Figure 12B:
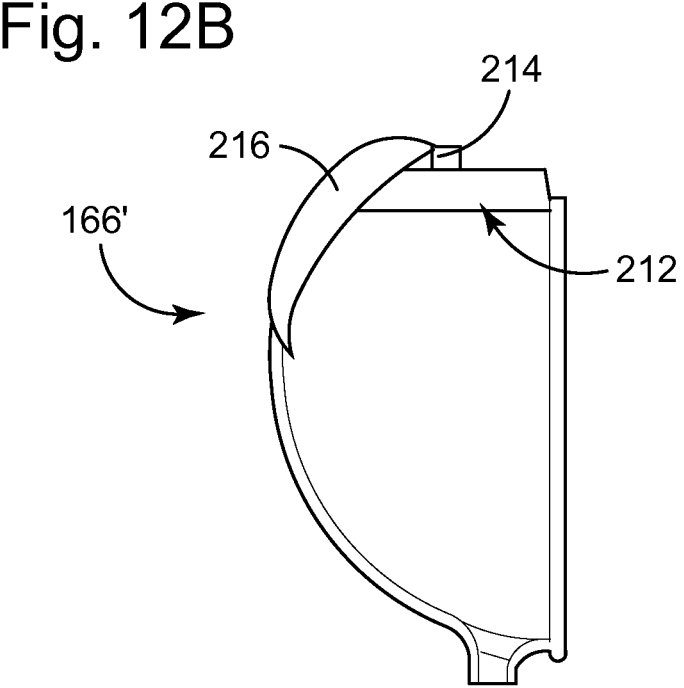
FIG. 12B is a side view of the milk container of FIG. 12A after the handle has been actuated by a user such that the expandable portion is in an expanded position.

FIGS. 12A and 12B illustrate a collection mechanism 166' having features that allow a user to selectively apply a vacuum force to a nipple and areola of a breast. A top portion 210 of the collection cap 166 can include an expandable piece 212 that can expand the volume inside the collection cap 166 and create a constant vacuum; the expandable piece 212 being coupled to a rod 214 coupled to a handle 216. The expandable piece 212 can be positioned on an opposite side of the port 190, which is disposed at a bottom of the collection cap 166, and can form an expandable chamber. The expandable chamber can be a dome-like pocket shown in FIGS. 12A and 12B. A volume of the chamber 212 can be increased and decreased by movement of the handle 216, which can actuate a pumping mechanism that changes a volume of the vacuum chamber. This change in volume creates air pressure changes in the interior of the collection cap 166 and helps conveys milk expressed from a breast.

Figure 13:
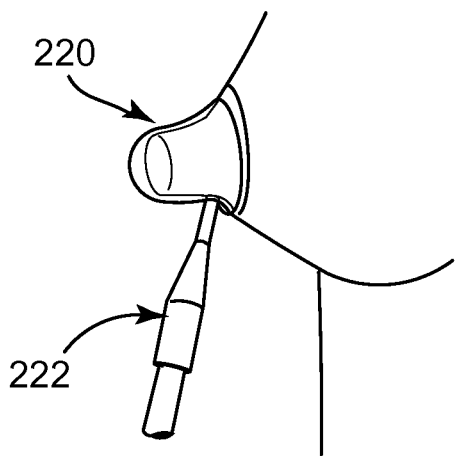
FIG. 13 is a perspective view of a nipple cap for stimulating milk expression.
Figure 14A:
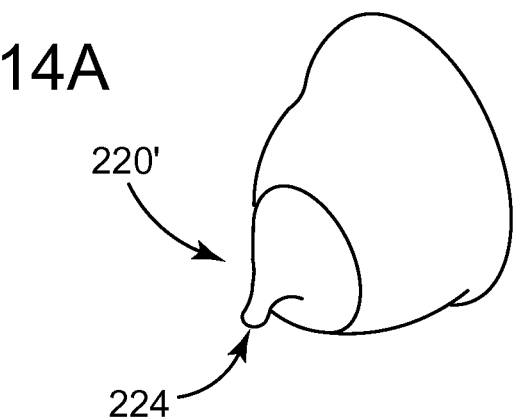
FIG. 14A is an exemplary embodiment of a nipple shield having an exit port formed therein.
Figure 14B:
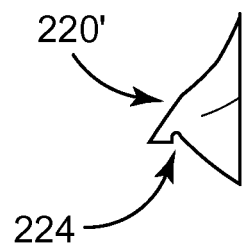
FIG. 14B is a side view of the nipple shield of FIG. 15A.

A milk expression system can include other components that facilitate expression, collection, and transport of expressed milk. For example, FIG. 13 illustrates a tight-fitting nipple cap 220 in which a constant vacuum can be applied to a nipple by drawing air from the cap 220 into a syringe 222. The nipple cap 220 can be substantially spherical or substantially cylindrical shaped to accommodate varying nipple diameters and lengths and can include an opening and a base that is positioned over or adjacent to an areola. The nipple cap 220 can include one or more ports 224 formed therein for transporting expressed milk or the nipple cap 220 can be formed from a fluid permeable material. FIGS. 14A and 14B illustrate nipple shields 220' that can be used with or without an applied vacuum and can be used either with the milk container embodiment 166 or by itself (e.g., in place of the milk container, held in place with a strap and ultimately, connecting directly into a collection bag). Similar to the nipple cap 220, the shields 220' can include a base positioned over or adjacent to an areola. The base can be shaped in various ways, but is shown having a substantially circular shape. The nipple shields 220' can have a tapered shape moving from the areola to a terminal end of the nipple, and can include at least one exit port 224 formed in a terminal end of the nipple shield 220'. The at least one exit port 224 can be angled down, as shown, so that gravity facilitates collection of milk. The nipple shields 220' can be releasably coupled to a nipple and/or areola in various ways, such as through elastic clips attached to the base of the initializing component or bra of held in place by the force and adjustability of a milk collection cap system. The addition of the milk collection cap 166 can also help to smooth the appearance of the nipple shield 220'. The nipple shields 220' can form a seal with the nipple via pressure, vacuum, elastic material on a portion of the bra, etc.

The component that collects milk directly from a nipple (such as a nipple shield and/or milk collection cap) can couple to a milk-transporting mechanism, e.g. a tube. These components can either be one continuous material, or independent pieces that are selectively connected and detached by the user. In one embodiment, the milk-transporting mechanism can be a tube (not shown) that may be straight or curved, the tube having an inner surface formed of a hydrophobic material. The tube can be substantially rigid, but is preferably substantially flexible to allow a user to selectively reposition the tube relative to other components. The milk-transporting component may be adapted to include a Y shaped port at a nipple shield so that the air exhaust from the solenoid, if present in an electrically powered pumping system, can be used to push milk down into the storage bag. Two separate tubes can be used to transport expressed milk from the left and right breasts independently to two separate milk storage containers, or two lengths of tube can merge into one single tube for final transport into a single storage container.

FIGS. 15-22 illustrate milk expression systems and various components thereof that do not include a clamping component that extends across a superior portion of a breast, and instead include initializing components for compressing a base of a breast and compressing components for compressing portions of a breast between the initializing component and an areola. This initializing and compression can be accomplished in various ways, such as using multiple inflatable bladders. As will be appreciated by those skilled in the art, the systems discussed below can include any combination of features described above, such as a milk collection container, nipple shield, and associated attachment mechanisms, and can be used to apply constant or cyclical pressure to various portions of a breast.

Figure 15A:
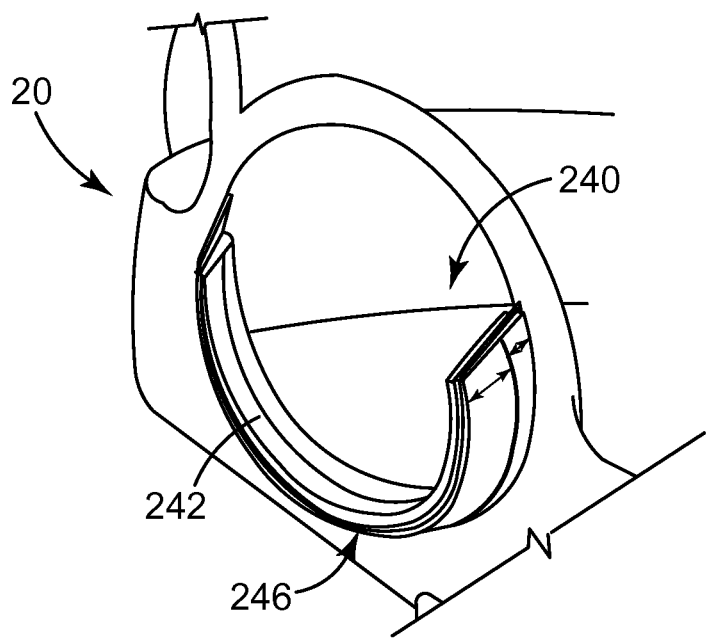
FIG. 15A is a perspective view of another exemplary initializing component coupled to an opening in the brassiere.

FIG. 15A illustrates another embodiment of an initializing component disposed on a bra. In this embodiment, the initializing component 240 is substantially U-shaped and includes an inflatable bladder 242 that can directly contact a breast and an outer portion 246 that couples the initializing component to the bra 20, supports a breast similar to underwire, and does not directly contact a breast. The outer portion 246 of the initializing component 240 can act as a rigid substrate in which to secure the bladder 242 so that outward expansion is not visualized and so that compressing motions remain discreet. The outer portion 246 of the initializing component 240 can include one or more attachment mechanisms (not shown) for coupling to other components of the system, such as Velcro. The outer portion 246 can be substantially rigid and can be formed from various materials, such as nylon, lycra, hardened rubber, plastic, or any other FDA approved inelastic material.

Figure 15B:
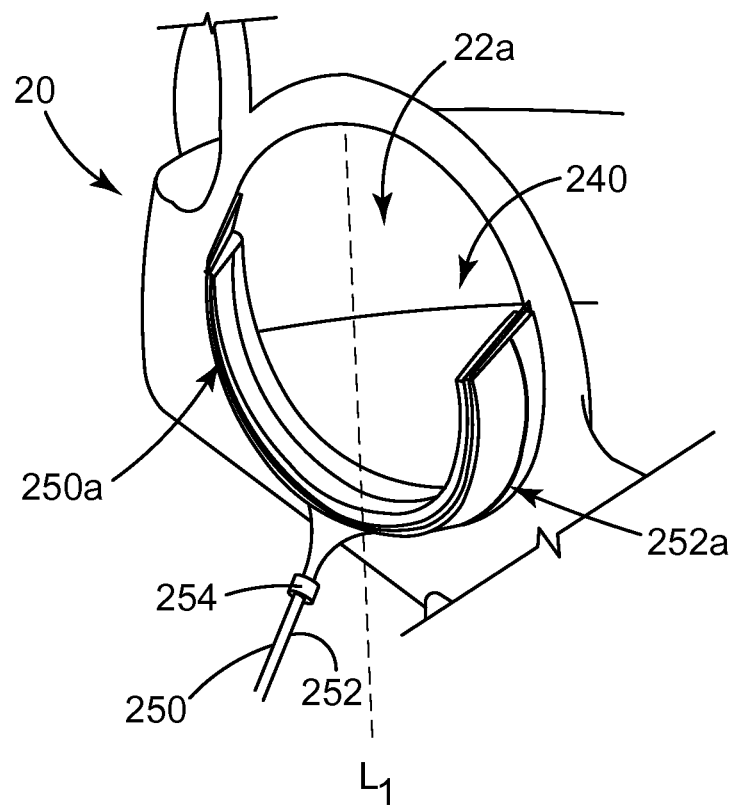
FIG. 15B is a perspective view of a mechanism for adjusting a size of a compression element.

A milk expression system can have various mechanisms for allowing adjustability of the initializing component around a user's breast. This includes by way of non-limiting example, a ratchet system with a quick release, clasps, Velcro, snaps, etc. The initializing component may also be reinforced by adjustable, rigid components that attach at the bottom of the initializing component underneath each breast, such as using a ratchet system with a quick release, clasps, Velcro, snaps, or any other mechanism that allows for adjustability. In certain aspects, these adjustment mechanisms may circle around the back of a user or over a user's shoulders similar to a standard brassiere. For example, FIG. 15B illustrates the initializing component 240 of FIG. 15A having an adjustment mechanism 248 that includes two lengths of wire or string 250, 252 that are joined together and extend through a slidable holder 254. A terminal end 250a of the first string 250 can be coupled to the outer portion 245 of the initializing component 240 and positioned on a first side of a central longitudinal axis $L_1$ dividing the opening. A terminal end 252a of the second string 252 can be coupled to the outer portion 246 of the initializing component 240 and on a second side of the central longitudinal axis $L_1$. The terminal ends 250a, 252a of the string 250, 252 can be located at any position around the outer portion 246 of the initializing component 240, but positioning the terminal ends closest to first and second terminal ends of the initializing component 240 can allow for greater control over adjustment to fit a breast. The slidable holder 254 can include frictional features (not shown) configured to hold the lengths of string in a desired position. The slidable holder 252 can be manually moved toward the outer portion 246 and can directly contact the outer housing, causing the initializing component 240 to adjust to a size and shape of a breast disposed in the opening 22*a*. The slidable holder 252 can also move independently along each of the first and second strings to allow for further customization around a breast, i.e. tightening or loosening a single side of the initializing component 240.

Figure 16:
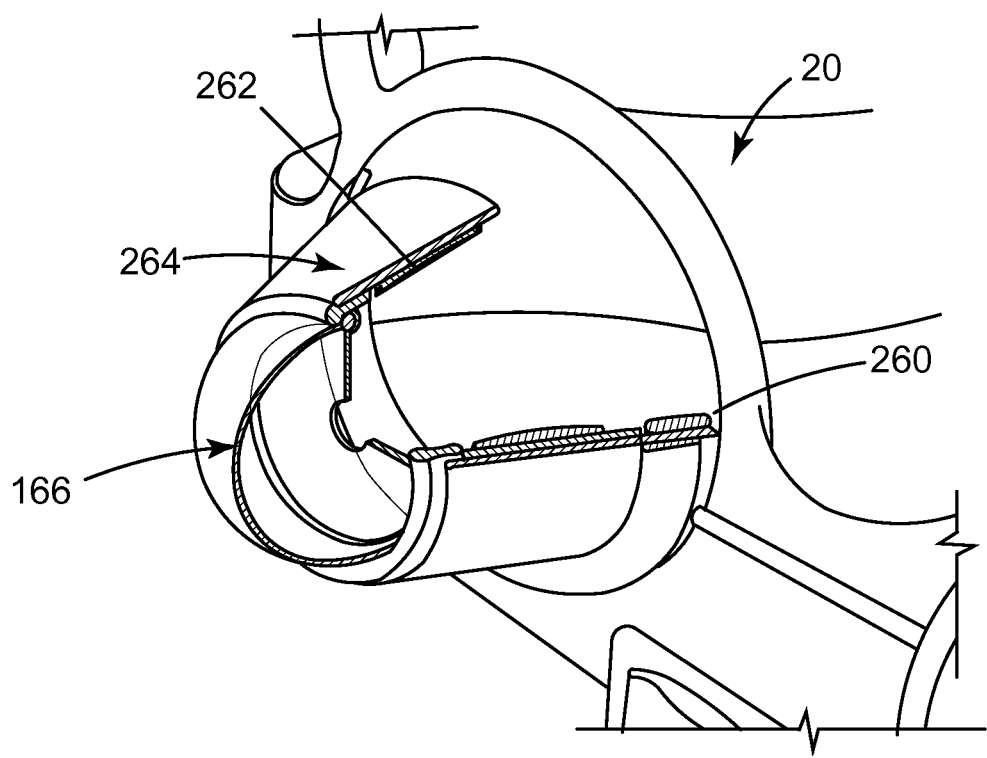
FIG. 16 is a perspective view of another exemplary initializing component disposed on a brassiere, the initializing component configured to extend partially around a circumference a breast and serving as an attachment point for a bladder.

In a system having at least two inflatable bladders per breast, the bladders can be positioned at various locations along the breast. For example, a first bladder can be positioned at the base of the breast and can act as an initializing component while a second bladder can be positioned adjacent to the areola. Such an arrangement is shown in FIG. 16, which includes an initializing component, i.e. initializing bladder 260, and a compression mechanism, i.e. a compression bladder 262. In the illustrated embodiment, the bladders 260, 262 extend partially around a circumference of a breast such that the bladders 260, 262 do not contact a top, sloped portion of a breast. As in other embodiments, a substantially rigid housing 264 can extend around the opening in the bra 20 and can act as a privacy barrier. In other embodiments, one or more of the bladders can extend around an entire circumference of a breast. The bladders 260, 262 can be inflated in various ways. For example, the bladders closest to the base of the breast can be inflated first and the bladders closest to the areola can be inflated after to sequentially stimulate the milk ducts. In another example, the bladders can be inflated and deflated simultaneously. In yet another example, the initializing bladder 260 closest to a chest wall can be inflated to a constant pressure and then the compression bladder 262 can be inflated and deflated in a cyclical manner to facilitate milk expression. The bladders 260, 262 can be positioned at various angles on a breast, such as axially aligned with a chest wall or angled relative to a chest wall.

Figure 17A:
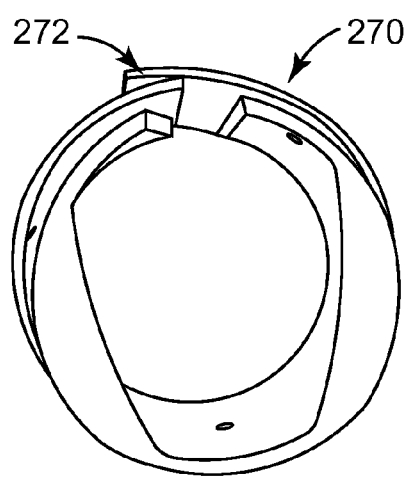
FIG. 17A is a perspective view of a housing for holding an inflatable bladder therein.
Figure 17B:
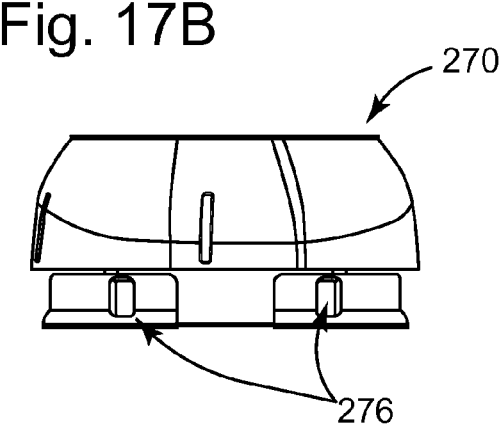
FIG. 17B is a side view of the housing of FIG. 17A.
Figure 17C:
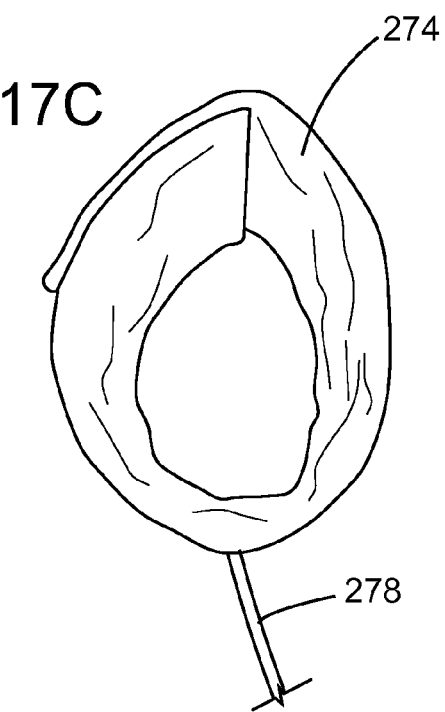
FIG. 17C is an exemplary bladder that can be inserted into the housing of FIG. 17A.

The initializing component can vary in any number of ways. For example, an initializing component 270 can have two rigid sections that pivot at the bottom base of the breast and can be tightened by pulling them together at the top of the breast, as shown in FIGS. 17A-17C. The initializing component 270 can be tightened on a breast by adjustable inelastic components 272 that attach at the top of the initializing component above each breast (using a ratchet system with a quick release, clasps, Velcro, snaps, or any other mechanism that allows for adjustability) and circles around the neck to tightly secure the component to the base of the breast and prevent the initializing component 270 from slipping down the sloped portion of the breast. FIGS. 17A-17C illustrate another embodiment of an initializing component 270 that includes an inflatable bladder 274 and the housing 270 that acts as a privacy barrier. As shown in FIG. 17A, the housing 270 can be configured to extend around an entire circumference of a breast. The housing 270 can be formed from a substantially rigid material so as to allow the housing 270 to act as a privacy barrier for preventing visible movement of the housing 270 as the bladder 274 is inflated. The housing 270 can be shaped in various ways, but as shown has a substantially circular opening for receiving a breast therein. As shown in FIG. 17B, the housing can be adjustable to custom fit a breast, such as via one or more adjustment mechanisms 276 disposed thereon. Large breasts can have little overlap of the right and left side of the housing 270, while small breasts can have considerable overlap. Velcro, buttons, magnets or any other securing mechanism can be used to hold the housing in place at the correct size. The housing 270 can be configured to receive one or more inflatable bladders therein, such as the inflatable bladder 274 shown in FIG. 17C. The inflatable bladder 274 can include an input port (not shown) in fluid communication with a tube 278 for delivering inflation fluid to the inflatable bladder 274. One or more of the inflatable bladders can be positioned in direct contact with a breast and the housing 270 can be disposed therearound. The housing 270 can be coupled to a bra structure, as in the previous embodiments, or can be selectively attached and detached from a breast without the use of the custom bra structure. Any number of inflatable bladders can be positioned at any location along a user's breast, from a base of the breast to an area adjacent to an areola. The bladder(s) can be positioned at various angles on a breast, such as axially aligned with a chest wall or angled relative to a chest wall.

Figure 18A:
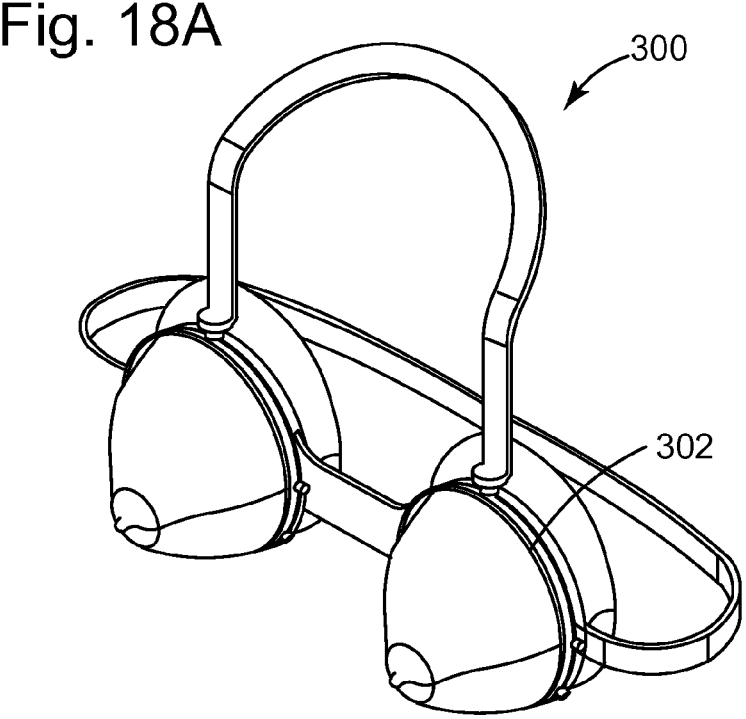
FIG. 18A is a perspective view of another exemplary milk expression system in the form of a brassiere.
Figure 18B:
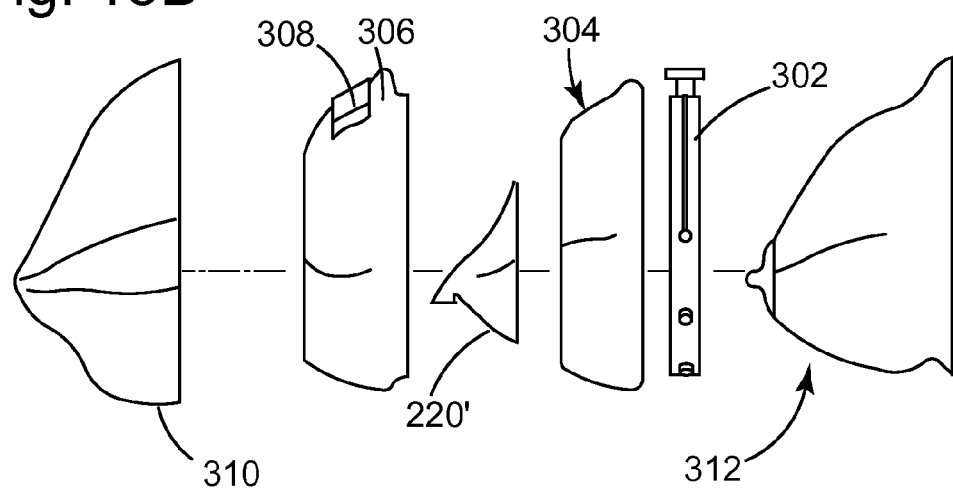
FIG. 18B is an exploded view of the system of FIG. 18A, including an adjustable initializing component, an inflatable bladder, a milk collecting nipple shield, and various layers for covering a breast.

Another embodiment of a milk expression system 300 is shown in FIGS. 18A-18B. The milk expression system 300 can include an initializing component 302 and a compression mechanism 304. The initializing component 302 can have various configurations, but in the illustrated embodiment is substantially rigid ring-shaped member. As previously mentioned, an expression system can generally include a compression mechanism that can be positioned adjacent to an areola. As shown in FIG. 18B, the compression mechanism can be a first inflatable bladder 304 that can be positioned adjacent to the initializing component 302 and/or adjacent to an areola/nipple shield 220' disposed on an areola. The first inflatable bladder 304 can have one or more attachment mechanisms for coupling the inflatable bladder 304 to the initialization component 302. A bladder cover 306 can be substantially the same shape as the inflatable bladder 304 but slightly larger so that the cover can be positioned over the bladder 304 and act as a privacy barrier to limit movement that would be visible to others when the system is expressing milk. The bladder cover 306 can also include one or more attachment mechanisms 308 for coupling the cover to an optional bra cover 310. The bra cover 310 can be generally sized and shaped to correspond with a size and shape of a breast 312, as shown, but can be formed from soft material to increase a user's comfort. Additionally, the bra cover 310 can be configured to allow a tube or milk collection container (not shown) to extend beneath the cover 310 so that the tube/collection container can have access to and be coupled to the nipple shield 220' to allow collection of expressed milk. As in the previous embodiments, the nipple shield 220' and/or the nipple alone can be directly coupled to a vacuum, and this can increase milk output.

Figure 19A:
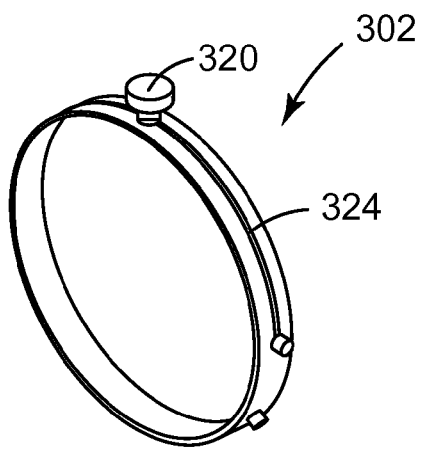
FIG. 19A is a perspective view of a ring-shaped initializing component.
Figure 19B:
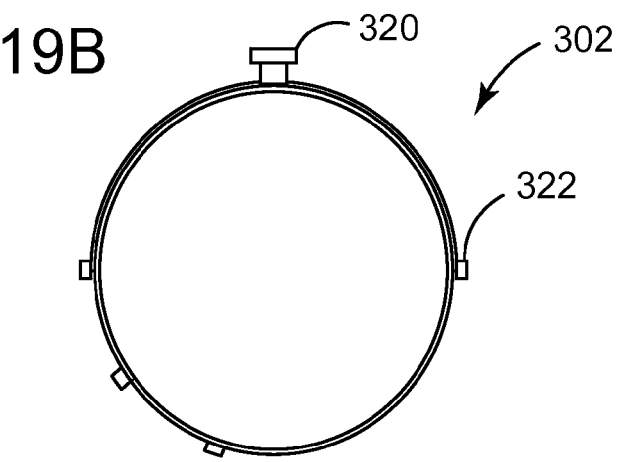
FIG. 19B is a front view of the ring-shaped initializing component of FIG. 19A.
Figure 19C:
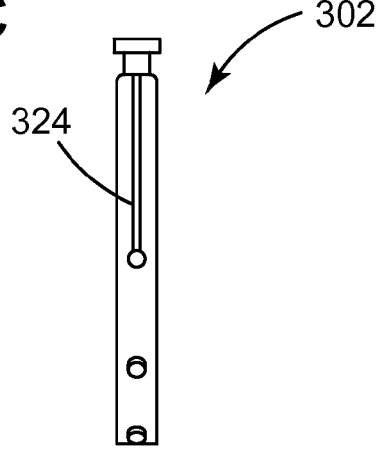
FIG. 19C is a side view of the ring-shaped initializing component of FIG. 19B.

As in the previously described initializing components, the initializing component in FIGS. 19A-19C can have various sizes, shapes, and configurations. In general, the initializing component 302 can be adjustable to fit a variety of sized breasts via one or more adjustment mechanisms. The adjustment mechanism can vary and can be a strap, ratcheting system, spring loaded, or other adjustment mechanism known in the art. As shown, the initializing component 302 can include an adjustment knob 320 that can be located above the breast for easy access. The adjustment knob 320 can be located at various positions around a breast such as below or on either side of a breast. The initializing components 302 can be disposed around and directly contact a circumference of a breast and can be attached to a strap that extends across a user's chest and around a user's back, as shown in FIG. 18A. The adjustment knob 320 can be coupled to a wire 324 extending within and around an outer housing of the initializing component 302 such that rotation of the knob 320 can increase or decrease a diameter of the wire 324. In use, the adjustment knob 320 can allow the initializing component 302 to be in a compressed position that applies a substantially constant pressure to a base of a breast. However, a user can also increase or decrease a pressure applied by the initializing component 302 by rotating the knob 320 to facilitate comfort and/or increase or decrease a flow rate of expressed milk. The initializing component 302 can include various features for attaching the initializing component 302 to other components of an expression system. For example, the initializing component can include one or more protrusions 322 configured to mate with a user's regular bra or to mate with a bra specifically designed to receive the initializing component 302 therein. The protrusions 322 can be configured to attach to the initializing component to the bra structure. In another embodiment, the initialization component can be positioned directly against a breast and added to a user's own bra.

Figure 20A:
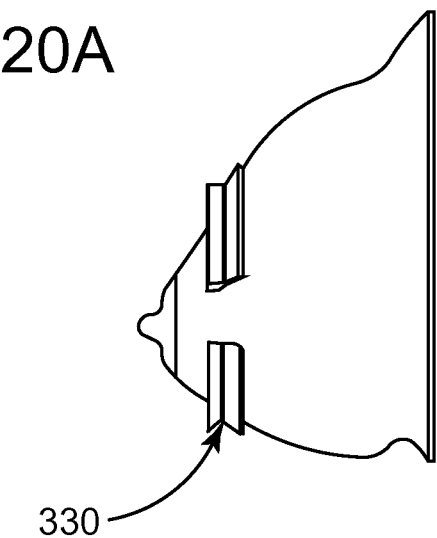
FIG. 20A is side view of rigid compression element disposed around a breast, adjacent to an areola.
Figure 20B:
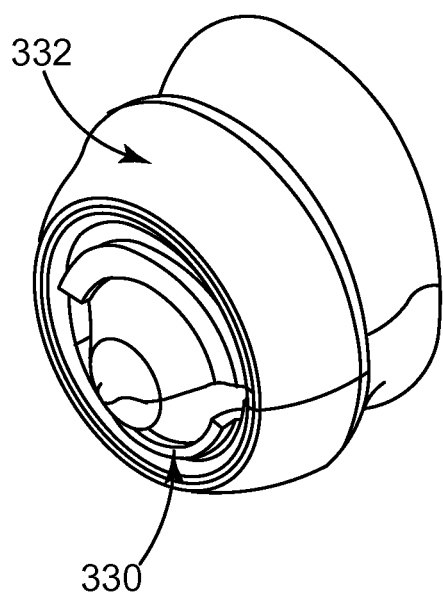
FIG. 20B is a perspective view of the rigid compression element of FIG. 20A disposed around a breast and having a housing positioned therearound.

The milk expression system can have various compression mechanisms in addition to or as an alternative to the inflatable bladder 304 shown in FIG. 18B. For example, the expression system can be used with a clamp 330, as shown in FIGS. 20A and 20B, located at the base of the breast and creating a force against a clamp 330 at the end of the breast near the transition to the areola. The breast clamp 330 can have various sizes, shapes, and configurations. This clamp 330 or other similarly shaped pieces localized around the nipple may also include additional nipple stimulation such as vibration, heat, or other stimulating mechanisms. In the illustrated embodiment, the clamp 330 is a substantially C-shaped member configured to be positioned on a breast in proximity to an areola, such as about 0.5 inches away from an areola measured from the areola in a direction toward a chest wall. The clamp 330 can form a substantially circular opening having an inner diameter in the range of about 1 to 10 inches. In another embodiment shown in FIG. 20B, the compression mechanism can further include an outer bladder (not shown) and a housing 332 disposed around a circumference of the clamp 330 to. This outer bladder can apply additional cyclical or constant compression uniformly around a circumference of the clamp 330 and the housing 332 can prevent movement of the bladder 330 from being visible to others.

Figure 21A:
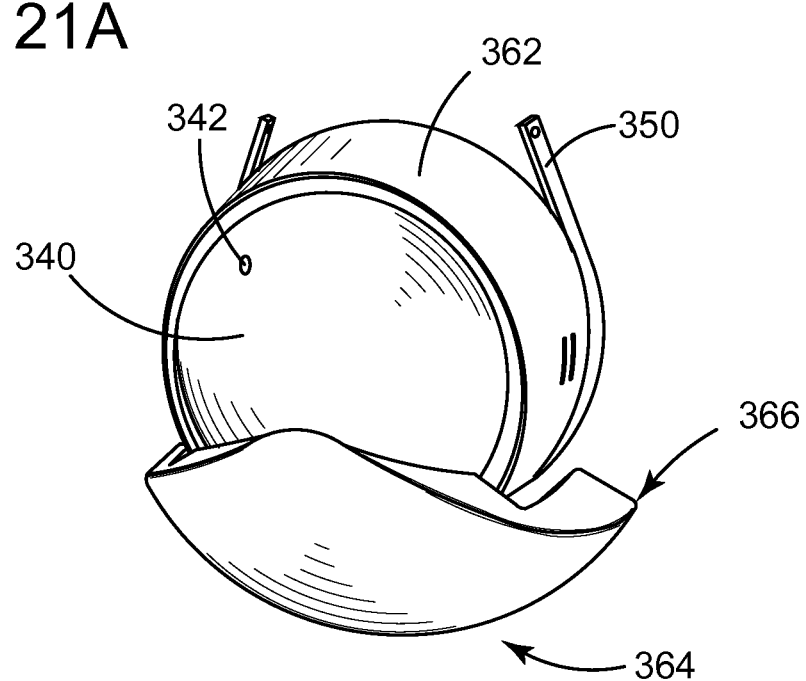
FIG. 21A is a perspective view another exemplary milk expression system having a single inflatable compression member disposed in a housing and having a contoured milk container coupled thereto, the milk container being contoured so that it can be positioned along a lower portion of a user's breast.
Figure 21B:
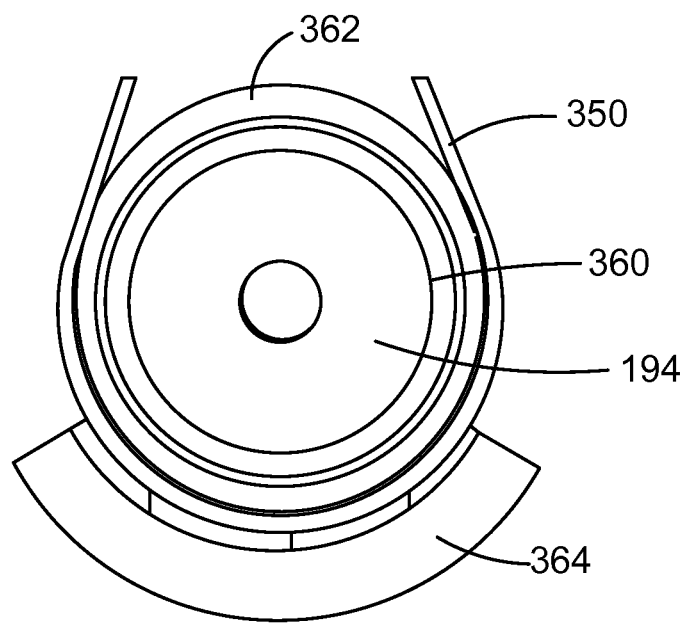
FIG. 21B is a perspective view of a side of the housing of FIG. 21A that includes an opening for receiving a nipple therein.

Another embodiment of an expression system is shown in FIGS. 21A-21B. This expression system can be used with any regular bra as an "add-in" prior to expressing milk. This system is compression-based and includes an initialization component 350 and a compression member 360, similar to the previous embodiments. This system can also have a constant vacuum that would include a dual compression and vacuum pump (not shown) for applying a vacuum to a nipple. In this embodiment, a collection cap 340 can include a hole 342 formed therein, shown in FIG. 21A near a top portion of the collection cap 340. When a vacuum system is used, air can be removed from the collection cap 340 at the hole 342 to create a vacuum. In FIG. 21, the initializing component 350 is a substantially U-shaped member that can be joined with a strap or other tightening mechanism (not shown) to create a constant compression at the base of a breast and secure the expression system to a user's breast and/or own bra. An inflatable bladder 360 can be positioned in a housing 362, the housing 362 being a substantially rigid ring-shaped member that acts as a privacy barrier for preventing movement of the bladder 360 from being visible to others. The collection cap 340 can mate with the housing 362 via any known attachment mechanism known in the art. The collection cap 340 can include a milk collection container 364 that is integrally formed as a unitary structure, as shown in FIG. 21A. As shown, the container 364 is shaped to correspond with a bottom, inferior portion of a breast. That is, a width of the container 364 increases moving from a top portion down toward a bottom of the housing 362. A bottom portion 366 of the container 364 can extend below the housing such that the container has a substantially triangular cross-sectional shape. This curved profile of the milk collection container 364 can cause milk to flow downward during expression because of gravity. A flexible cover or membrane 194 can be sized, shaped, and configured to connect to the milk collection cap 340 and can receive a nipple therethrough. The flexible membrane 194 shown in FIG. 21B can have any or all of the features described with respect to the flexible membrane in FIG. 11B. In this exemplary embodiment, the milk collection container 364 can be the only piece that comes in contact with breast milk, compared with existing vacuum pump designs that can have multiple pieces in contact with breast milk and all require cleaning. Any or all of the components in contact with the milk can be made from any material FDA approved for use in a breast pump, such as polypropylene or PVC.

Figure 22A:
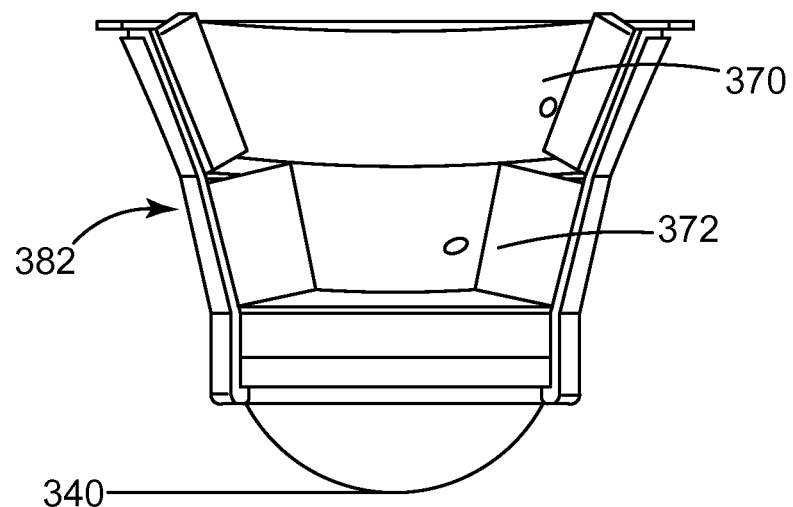
FIG. 22A is a top view of another exemplary embodiment of a housing for receiving a breast that includes a first initializing bladder and a second compressing bladder.
Figure 22B:
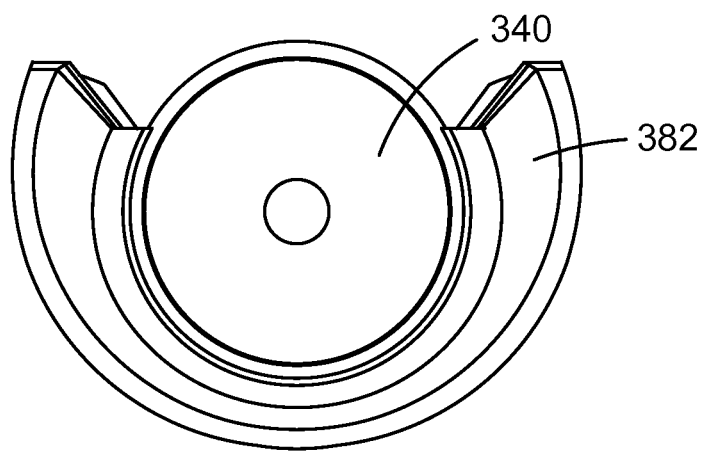
FIG. 22B is a front, perspective view of the housing of FIG. 22A.
Figure 23A:
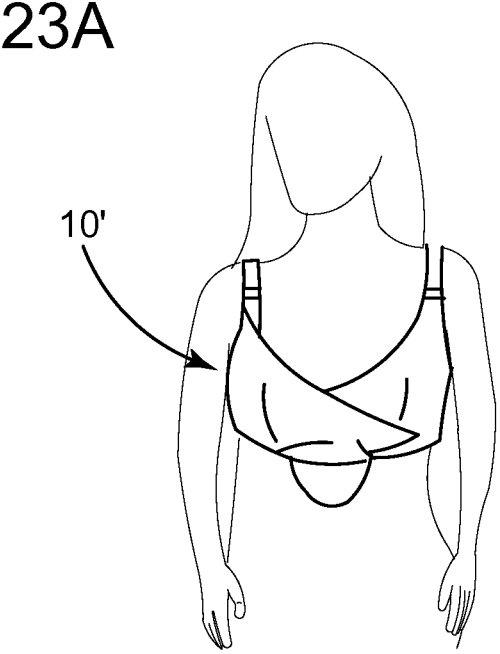
FIG. 23A is a perspective view of a compression-based accessory system in the form of a brassiere worn by a user that can be coupled to a conventional vacuum-based breast pump, the accessory system allowing for hands-free milk expression.
Figure 23B:
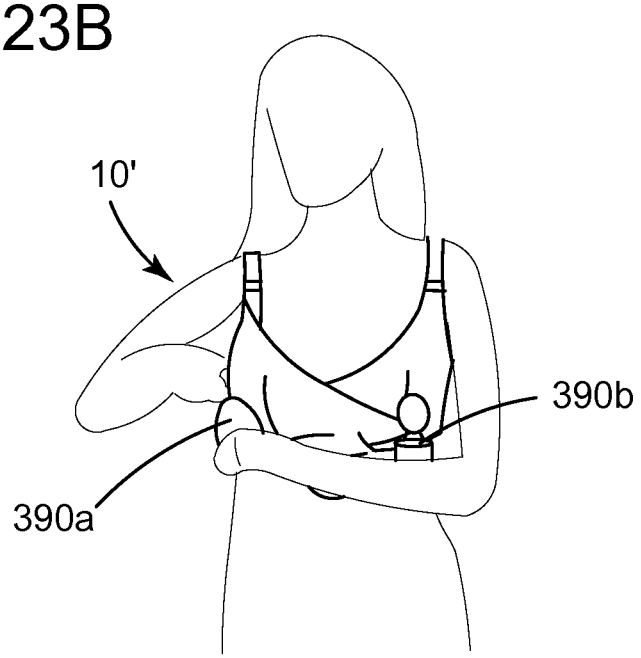
FIG. 23B is a perspective view of the system of FIG. 23A including first and second milk collection containers of a standard vacuum-based breast pump.
Figure 23C:
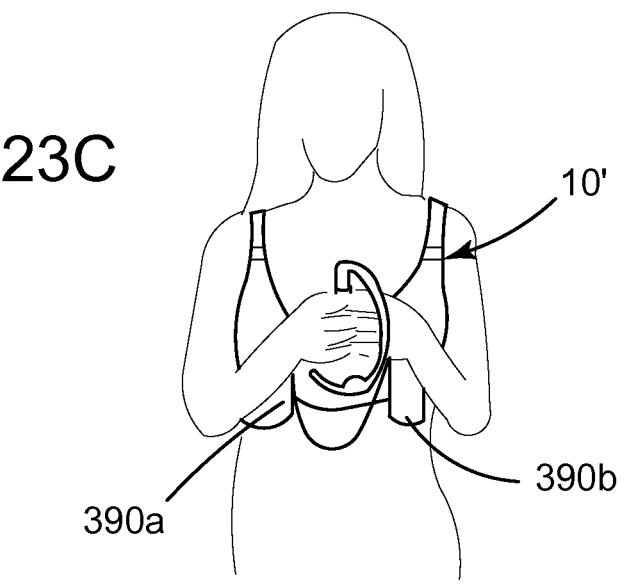
FIG. 23C is a perspective view of the system of FIG. 23A including a controller operable by a user.
Figure 23D:
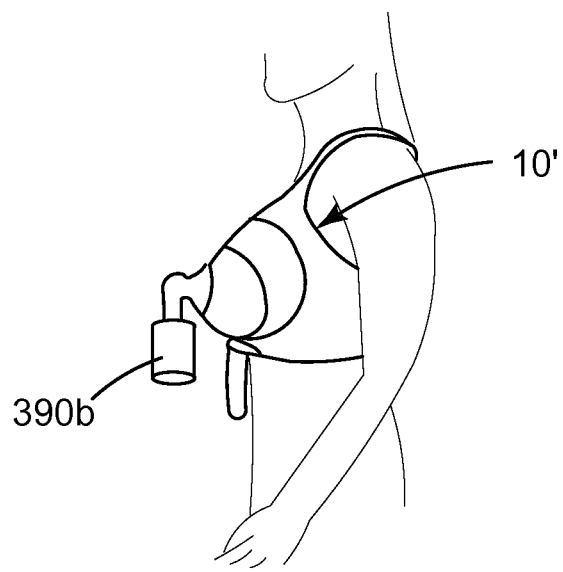
FIG. 23D is a side view of the system of FIG. 23A having an initializing component and milk collection container from a standard vacuum-based breast pump coupled to a user's brassiere.

Another embodiment of a milk expression system is shown in FIGS. 22A-22B. In this embodiment, the initializing component can be a second bladder 370 that is inflated and held at a constant pressure throughout the milk expression, the second bladder 370 being disposed at a base of a breast and a first bladder 372 being disposed closer to an areola and acting as a compression mechanism. Both of the first and second bladders 370, 372 can be disposed in a housing similar to the housing in FIGS. 21A-21B, but having a tapered profile from a milk collection cap 340 and to a base of a housing 382 that would be positioned against a user's chest. As in the previous embodiments, the housing 382 can be substantially rigid and can act as a privacy barrier. As shown in FIG. 22A, the first and second bladders 370, 372 can be positioned in directly contact with one another, in the housing 382. The first bladder can have a first width and the second bladder can have a second width, and the bladders can have any or all of the features described above with respect to the other milk expression systems. The positioning of the bladders within the housing can vary. The bladders can be spaced apart within the housing and thus would be spaced apart along a breast.

Components described herein can be modular so that they can be used in conjunction with conventional pumping/nursing bras. In this embodiment, as shown in FIGS. 23A-23D, a bra 10' can be adapted at the areola to hold the weight of milk collection bottles 390a, 390b of standard, FDA-cleared vacuum breast pumps. Any of the initialization or compressing components described above, such as a rigid ring-shaped member, an inflatable bladder, and/or a clamping component, can be disposed in or releasably coupled to the bra 10' and can stimulate a portion of a breast to improve milk output, including flow rate of milk and total milk volume. In another embodiment, by using a bra structure and a built in initializing component and modifying the bra cup design to allow for structured support of vacuum breast pump flanges at the nipple interface, the system can allow for hands-free compression added to a vacuum pump, which can increase milk output.

Figure 24:
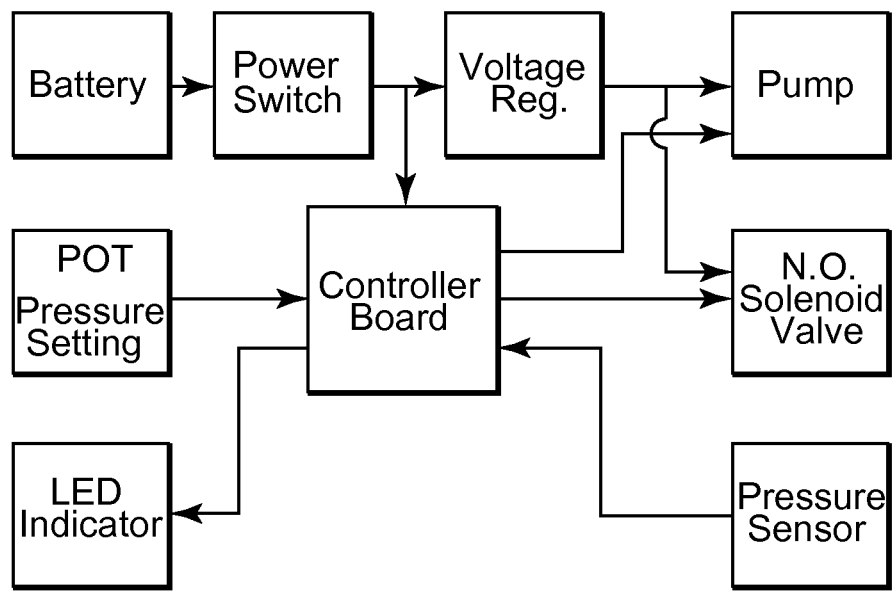
FIG. 24 is a block diagram of a controller interacting with various components of a milk expression system.

The milk expression systems herein can include a control system such as for operating a pump that controls movement of air and fluid into or out of the compression mechanism(s), e.g. one or more inflatable bladders. The system can include various components, such as a power source, control board, pump, sensors, etc, as shown in FIG. 24. All components can be low voltage and have low power consumption. The system can be powered in various ways, such as battery-powered or powered by a standard 115 V AC power supply. The control board can be powered by a low voltage (<12 V DC) rechargeable battery. The compressor can run continuously based on a manually operated on/off switch. The battery can supply power to a miniature pressure transmitter, miniature on/off light, miniature compressor, miniature solenoid/exhaust valve, one or more timers, and one or more pressure sensors. The voltage regulator shown is optional and may not be needed. The POT is a potentiometer used to adjust the pressure at which the solenoid valve exhausts. The LED indicator can be used to indicate pump operation or power switch position. The controller board can be programmed to cycle the pump on and off, and/or cycle the solenoid valve open/close based on inputs form the pressure sensor and the potentiometer. As an alternative to an electronic pressure sensor, a piston that is moved by the air pressure may include an adjustable spring to allow the piston to move differently based on the user adjusted spring location therefore allowing the air to exhaust at various pressure ranges and eliminating the need of an electronic pressure sensor. This piston system can also act as a safety relieve valve for the compressed air system. A solenoid/exhaust valve can open periodically to release the pressure in the system, and the pressure set point at which the solenoid opens can be adjustable based on the pressure transmitter or pressure piston input with an external user adjustable control knob. In one exemplary embodiment, the controls can have multiple pre-set pressure values (i.e. high, medium, low). The intake and/or exhaust port of the exhaust valve can include a sound attenuation muffler or other similar sound deadening material. The exhaust port of the solenoid valve can contain a restriction, such as a variably sized orifice, in the air flow path for a slower depressurization period. The control board can include a program that provides automatic step increases in pressure as breasts may need more pressure as milk emptying or adaption occurs. Various control system components can be mounted in a casing with the on/off switch, timer, and indicator light(s) as well as the control knob(s) on the outside of the casing. The casing can include sound attenuation products such as insulation to limit noise, further facilitating concealable expression of milk. The casing of the control system can be disposed at various locations, such as discreetly incorporated into the undergarment or removably positioned in one or more holding mechanisms on the side or back of a custom brassiere. The casing of the control system which may contain the compressor, solenoid, control board, and all other components except the brassiere and bladder, can alternatively or additionally be worn on another part of the user's garments, such as clipped on a belt buckle or stored in a pocket. The brassiere and bladder system can be connected to this control system via flexible air tubing.

The control system can include an easy to visualize timer to aid a user in controlling the duration of time compressing the breasts. The control system can include a component that allows the user to set their baseline bladder inflation time for complete milk excretion. The user can then setup the pump such that it will automatically turn off if the inflation time exceeds the baseline time by a certain percentage. This feature can allow the pump to automatically turn off once the breast(s) have been emptied of milk.

Figure 25:
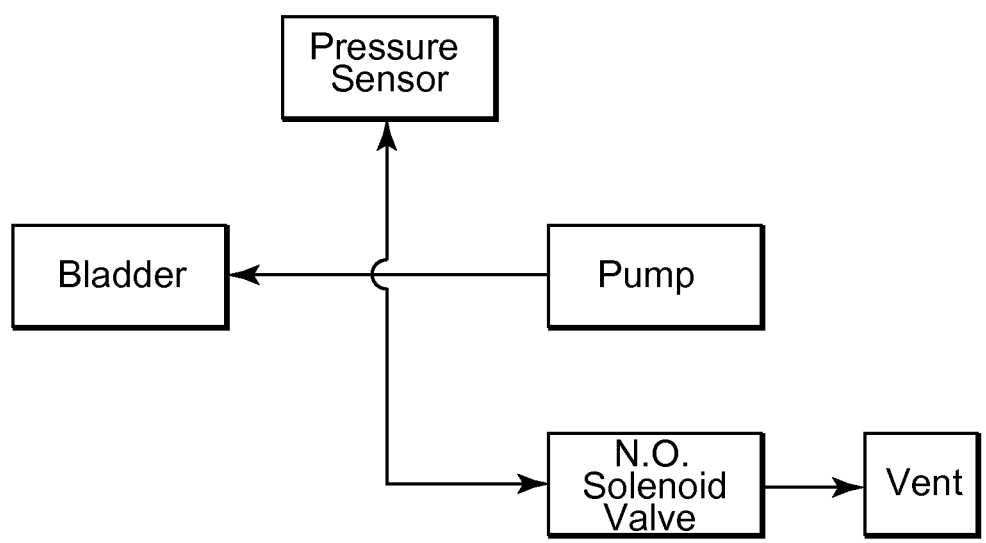
FIG. 25 is a block diagram illustrating a direction of air flow for an exemplary bladder that cyclically inflates and deflates due to opening and closing of a solenoid valve during continuous operation of a pump.

FIG. 25 shows an example of the air flow in which the solenoid valve cyclically exhausts based on the pressure sensor reading and the user adjusted pressure set point. The solenoid valve may open when the pressure set point is reached, then closes when the pressure falls to a pre-determined value (e.g. 2 psi) below the user adjusted set point. In certain aspects, the user can control to set the initial pressure on her breast prior to compression. The bladder can cyclically inflate/deflate due to the opening and closing of the solenoid valve during continuous operation of the pump.

Figure 26:
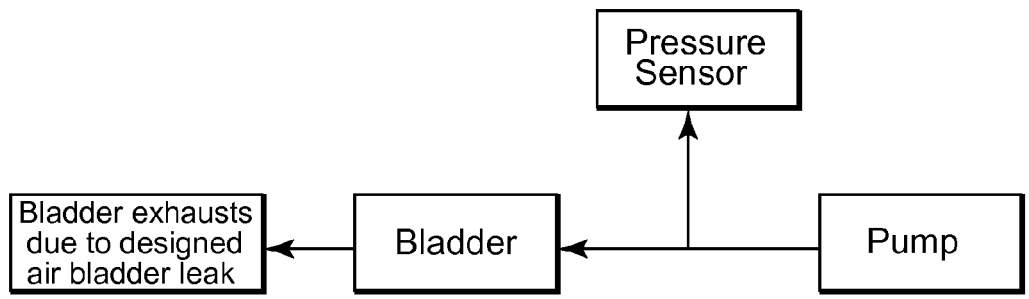
FIG. 26 is a block diagram illustrating air flow for an exemplary bladder designed to leak at a rate that permits cyclic compression of a breast.

FIG. 26 is a block diagram of air flow for an exemplary bladder designed to leak at a rate that permits cyclic compression of a breast. The pump flow rate can be higher than the bladder leak rate to ensure inflation. The cyclic motion can be created by cycling the pump on/off based on the pressure sensor reading.

Figure 27:
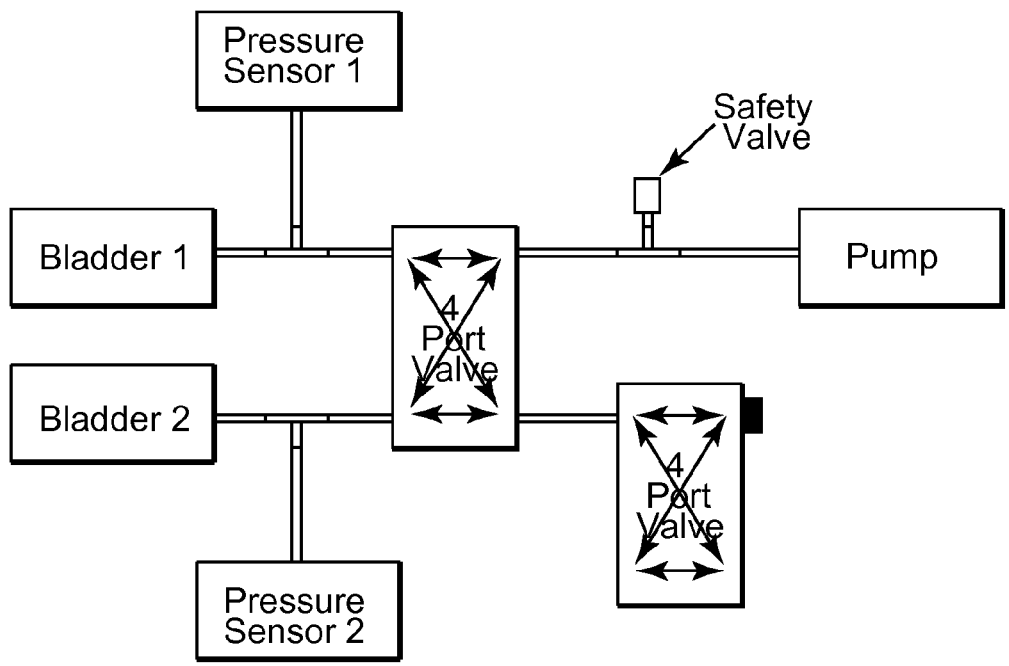
FIG. 27 is a block diagram illustrating an air flow path of a two bladder system, including an initializing bladder and a compression bladder.
Figure 28:
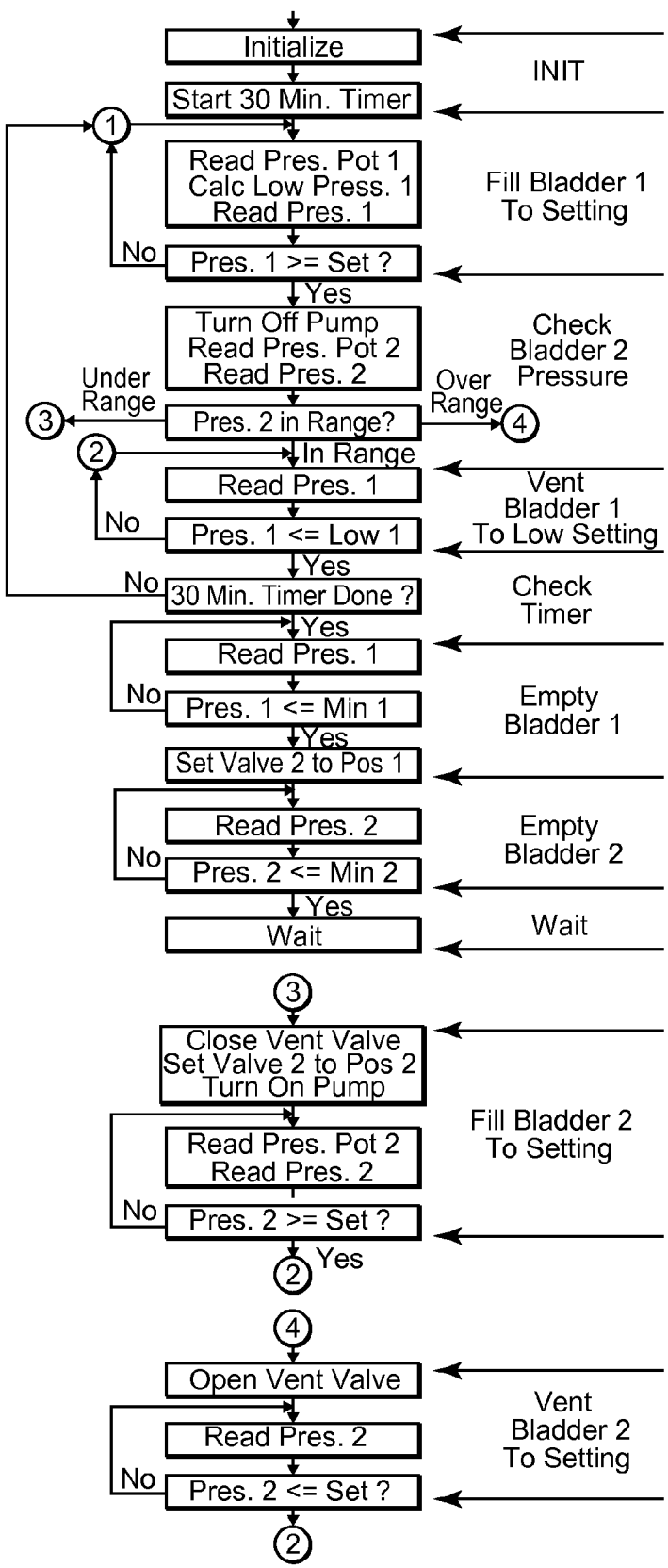
FIG. 28 is a diagram of a control scheme for a milk expression system having a cyclical compression bladder and an initializing bladder.

FIG. 27 illustrates the flow of fluid between a pump and other components for a milk expression system having first and second inflatable bladders. As shown, the system can include first and second pressure sensors, a first pressure sensor configured to measure a pressure in the first inflatable bladder and the second pressure sensor configured to measure a pressure in the second inflatable bladder. The initializing bladder can be inflated to a user adjusted pressure, then hold that pressure, while the compression bladder can cyclically inflate/deflate to a user adjusted pressure by exhausting the bladder through the second solenoid valve. The pump can operate to fill up bladder 1 to a user adjustable set pressure as measured by pressure sensor 1, then the 4 port valve can switch to direct the air flow into bladder 2 while holding bladder 1 at a constant pressure. Bladder 2 can then cycle between inflated & deflated by actuating the second valve open and closed based on the input from pressure sensor 2 and the user adjustable setpoint. The second valve is depicted as a 4 port valve, although a 2 or 3 port valve can also be used. A mechanical safety valve can be installed in this system or any other system to release pressure at a pre-determined set point. FIG. 28 illustrates a process control diagram for a milk expression system having first and second inflatable bladders. This control system methodology can ensure a constant pressure in bladder 1 while cycling pressure in bladder 2, as described above. The control system can continuously monitor both bladder pressures and keep both pressures in a user defined pressure range. The controls system may include a timer to automatically turn the pump off after a particular duration of time (depicted as 30 minutes).

A milk expression system can include various components that allow a user to control milk output and that facilitate overall ease of use. For example, a milk expression system can further include a temperature-sensitive component, which may be filled with a viscoelastic gel liner and surrounded by a comfortable, soft material that retains heat well, such as wool or silk. The temperature-sensitive component can be removable and can be positioned in contact with a breast in various ways, such as by being inserted inside a designed pocket in the brassiere, along a top of the breast. This material can be quickly heated in the microwave prior to initialization and compression to improve milk secretion. Due to the heat sensitive properties of the material, the user's own body heat can be trapped within the material's open cells and can continue to heat the breast tissue while it is in contact. As another example, in systems having one or more inflatable bladders, heated air can be used to fill the bladder to help elicit milk expression. More specifically, the compressor of the pump can be used to cycle heated air to the bladder to further support milk expression.

Alternatively or additionally, heat could be generated by lining various components in contact with the breast with insulating materials that will directly contact skin, such as wool disposed on inner surfaces of the bladders that directly contact a breast or on the strap shown in FIGS. 9A-9B that extends along a superior portion of a breast.

Various features can increase ease of use and for facilitating milk expression. A milk expression system can have a component that can be heated to improve milk secretion. A milk expression system can have a timer that displays elapsed time, and a controlled timer that can automatically stop activating milk expression when the flow rate of expressed milk has decreased, indicating that the breasts are emptied of milk. A milk expression system may also include a component that senses when the milk has reached a certain level in the bag to trigger an electronic signal to turn off the pump and stop the system from triggering milk expression. This includes a weight sensor to detect the maximum weight of milk the bag can withstand, a level sensor to detect when the liquid has reached a certain level and/or a temperature sensor to detect when a certain area of the bag has increased in temperature to a level that indicates milk collection, the temperature being in the range of about 98 to 101 degrees Fahrenheit.

The milk expression systems herein can include various combinations of components, but can be used in similar ways. An initializing component disposed in a bra structure can be positioned over a first breast and a second initializing component disposed in a bra structure can be positioned over a second breast. Alternatively, the initializing component can be disposed directly over a breast and need not be incorporated in a bra undergarment. The initializing component can be compressed against a base of a user's breast, adjacent to a chest wall in various ways, such as by adjusting a size of the initializing component by mechanical means (such as an adjustment knob of the initializing component of FIGS. 19A-19C). Alternatively, where the initializing component is an inflatable bladder, fluid can be delivered to inflate the inflatable bladder against a base of the breast by activating a pump. A clamping component can extend across a superior portion of a breast and can be manually adjusted so that it clamps down on the breast as an alternative type of initializing component. These size adjustment and pressure setting steps can be repeated for each breast. A user can adjust a pressure applied by the initializing component/clamping component in order to trigger a hormonal response, encouraging milk expression. A collection system can be coupled thereto and can include a milk collection container that receives expressed milk and any of the collection and containment mechanisms previously described. One or more compression mechanisms, such as a localized nipple clamp or any of the inflatable bladders previously described, can be positioned along and in contact with each breast. With the system in place coupled to a user, preferably, a hand pump can be used to inflate the initializing component and/or the compression mechanism to apply either a cyclical or a constant pressure at various locations on a breast. After expression has began, a user can use the hand pump to inflate the initializing component and/or the compression mechanism to accommodate for a decrease in breast size resulting from a volume of milk having been expelled from the breast. In another embodiment, an electrical pump can be activated so that the compression mechanism can apply cyclical or constant pressure to the breast at various locations on a breast. In general, these techniques can cause milk to be expressed and collected in one or more collection containers or collection bags. A vacuum can optionally be applied to one or more of the nipples to facilitate milk collection. One or more containers/bags can be manually detached from the expression system after the pump has been disengaged and a desired amount of milk has been collected. After milk expression is complete, a user may release the pressure initialization component to increase the brassiere's comfort level, facilitating wearability of the system when it is not actively used to express milk. In the case of a manual pump, when a user feels her breasts are empty, she can release the pressure by opening a valve that will deflate one or more of the inflatable components. After a desired amount of time wearing the system, for example, about 8-12 hours, components that contact milk can be detached, cleaned, and then reattached.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for expressing milk from a human breast, comprising:
    a brassiere having a first and second opening formed therein, the first opening configured to receive a first breast and the second opening being configured to receive a second breast;
    an initializing component positioned adjacent to at least one of the first and second openings and configured to apply pressure to a base of the received breast in the respective at least one of the first and second openings, including an inferior portion of the received breast and first and second lateral sides of the received breast, without applying direct pressure to any superior portion of the received breast; and
    a clamping component configured to apply a pressure to the received first or second breast, without applying direct pressure to any superior portion of the received first or second breast, and being sized and shaped such that when the first or second breast is disposed in the respective first or second opening, the clamping component extends across the inferior portion or the first and second lateral sides of the received first or second breast; and
    a milk collection mechanism configured to hold milk, the milk collection mechanism comprising a cap, a membrane configured to be coupled to the cap, and a hole for receiving milk from a nipple of the received first or second breast, wherein the milk collection mechanism is configured to be attached to the clamping component.

2. The system of claim 1, wherein the initializing component includes a protrusion integrally formed along a first terminal end of the clamping component.

3. The system of claim 1, wherein the milk collection mechanism collects and transports expressed milk to at least one containment mechanism that holds milk therein, the at least one containment mechanism being selectively detachable from the brassiere by a user.

4. The system of claim 3, wherein the membrane is substantially leak-proof and configured to create a seal around the nipple and an areola of the nipple.

5. The system of claim 4, wherein, when the system is positioned on the user, the milk collection mechanism is angled downward such that gravity facilitates milk collection into a one-way valve coupled to the at least one containment mechanism.

6. The system of claim 3, wherein the at least one containment mechanism includes a sensor to monitor a fill level to prevent overflow of milk from the at least one containment mechanism.

7. The system of claim 1, further comprising a support member disposed along the first opening and configured to releasably couple to the clamping component such that the clamping component extends along an outer surface of the support member.

8. The system of claim 7, wherein the support member includes a pocket to receive a temperature-sensitive component, wherein the temperature sensitive component increases a temperature of a breast to facilitate milk output.

9. The system of claim 1, wherein the clamping component is configured to be manually adjusted by a user such that the user can control an amount of pressure applied to the received breast during milk expression.

10. A system for expressing milk from a human breast, comprising:
- a brassiere having a first and second opening formed therein, the first opening configured to receive a first breast and the second opening configured to receive a second breast;
- a substantially U-shaped initializing component positioned adjacent to at least one of the first and second openings and configured to apply pressure to a base of the received breast in the respective first and second openings, including an inferior portion of the received breast and first and second lateral sides of the received breast, without the initializing component applying pressure to any superior portion of the received breast;
- a clamping component configured to apply a pressure to the received breast, without applying direct pressure to any superior portion of the received breast, and being sized and shaped such that when the first or second breast is disposed in the respective first or second openings, the clamping component extends across the inferior or lateral portion of the received breast in the respective first or second openings; and
- a milk collection mechanism configured to hold milk, the milk collection mechanism comprising a cap, a membrane configured to be coupled to the cap, and a hole for receiving milk from a nipple of the received breast, wherein the milk collection mechanism is configured to be attached to the clamping component.

11. A system for expressing milk from a human breast, comprising:
- a brassiere configured to be worn by a user and having first and second openings formed therein, the first opening configured to receive a first breast and the second opening being configured to receive a second breast;
- an initializing component positioned adjacent to at least one of the first and second openings and configured to apply pressure to a base of the received breast in the respective at least one of the first and second openings, including an inferior portion of the received breast and first and second lateral sides of the received breast, without apply direct pressure to any superior portion of the received breast;
- a clamping component configured to apply a pressure to the received breast and being sized and shaped such that when the received breast is disposed in the respective first and second openings, the clamping component extends across and applies pressure to inferior and lateral portions of the received breast without applying direct pressure to any superior portion of the received breast; and
- a milk collection mechanism configured to hold milk, the milk collection mechanism comprising a hemispherically shaped cap, a membrane with an opening for receiving a nipple of the received breast, the membrane configured to be coupled to the cap as milk is expressed from at least one of the received first or second breast, wherein the milk collection mechanism is configured to be attached to the clamping component such that, in an operative position, the membrane is flush with the clamping component.

12. The system of claim 11, wherein the initializing component is comprised of an inflatable bladder configured to be disposed around a circumference of the base of the first or second breast received in the respective at least one of the first and second openings.

13. The system of claim 12, wherein the inflatable bladder is encased in a housing having an outer surface that does not expand when the inflatable bladder is inflated.

14. The system of claim 11, wherein the initializing component includes at least one inflatable bladder configured to extend around a circumference of the received first or second breast, the initializing component configured to apply cyclical or constant pressure along a portion of the received first or second breast.

* * * * *